US012089867B2

(12) United States Patent
To et al.

(10) Patent No.: US 12,089,867 B2
(45) Date of Patent: Sep. 17, 2024

(54) TELESCOPING ATHERECTOMY DEVICE

(71) Applicant: AVANTEC VASCULAR CORPORATION, Sunnyvale, CA (US)

(72) Inventors: John To, Sunnyvale, CA (US); Paul Escudero, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 181 days.

(21) Appl. No.: 17/692,522

(22) Filed: Mar. 11, 2022

(65) Prior Publication Data
US 2022/0192698 A1 Jun. 23, 2022

Related U.S. Application Data

(63) Continuation of application No. 17/518,294, filed on Nov. 3, 2021, now Pat. No. 11,304,723.
(Continued)

(51) Int. Cl.
*A61B 17/3207* (2006.01)
*A61B 17/00* (2006.01)

(52) U.S. Cl.
CPC .......... *A61B 17/320725* (2013.01); *A61B 17/320758* (2013.01); *A61B 2017/00292* (2013.01); *A61B 2017/320733* (2013.01)

(58) Field of Classification Search
CPC .... A61B 17/320725; A61B 17/320758; A61B 2017/00292; A61B 2017/320733
See application file for complete search history.

(56) References Cited

U.S. PATENT DOCUMENTS

| 4,167,944 A | 9/1979 | Banko |
| 4,306,570 A | 12/1981 | Matthews |

(Continued)

FOREIGN PATENT DOCUMENTS

| EP | 0254414 | 8/1992 |
| EP | 0817594 | 3/1996 |

(Continued)

OTHER PUBLICATIONS

U.S. Appl. No. 63/126,847 (priority for U.S. Appl. No. 17/518,294, cited herein), To, et al.—owned by Applicant, filed Dec. 17, 2020.
(Continued)

*Primary Examiner* — Tuan V Nguyen
(74) *Attorney, Agent, or Firm* — Brian S. Boyer; SYNDICATED LAW, PC

(57) ABSTRACT

Telescoping, self-driving, and laterally-pushing atherectomy devices are provided, each having a flexible sheath, a cutter with helical flutes, and a drive assembly. The drive assembly can have a flexible driveshaft that is rotatably translational with the lumen of the flexible sheath, a positive displacement pump that begins pumping at the distal end of the drive shaft adjacent to the helical flutes at the proximal end of the cutter, and the flexible drive shaft can be longer than the flexible sheath to enable a reversible telescoping of the drive assembly from the lumen of the flexible sheath. The positive displacement pump can be a screw pump having a drive screw portion extending beyond the flexible sheath, exposed for contact with a vascular lumen for the self-driving. And, the devices can have a reversibly-expandable, lateral pushing member at the distal end of the flexible sheath for the lateral pushing.

17 Claims, 9 Drawing Sheets

Related U.S. Application Data

(60) Provisional application No. 63/197,970, filed on Jun. 7, 2021, provisional application No. 63/126,847, filed on Dec. 17, 2020.

(56) References Cited

U.S. PATENT DOCUMENTS

| | | |
|---|---|---|
| 4,445,509 A | 5/1984 | Auth |
| 4,598,710 A | 7/1986 | Kleinberg et al. |
| 4,598,716 A | 7/1986 | Hileman |
| 4,631,052 A | 12/1986 | Kensey |
| 4,669,469 A | 6/1987 | Gifford et al. |
| 4,690,140 A | 9/1987 | Mecca |
| 4,696,667 A | 9/1987 | Masch |
| 4,732,154 A | 3/1988 | Shiber |
| 4,770,652 A | 9/1988 | Mahurkar |
| 4,781,186 A | 11/1988 | Simpson et al. |
| 4,790,812 A | 12/1988 | Hawkins et al. |
| 4,804,364 A | 2/1989 | Dieras et al. |
| 4,808,153 A | 2/1989 | Parisi |
| 4,844,064 A | 7/1989 | Thimsen |
| 4,857,045 A | 8/1989 | Rydell |
| 4,857,046 A | 8/1989 | Stevens et al. |
| 4,867,157 A | 9/1989 | McGurk-Burleson |
| 4,886,490 A | 12/1989 | Shiber |
| 4,887,599 A | 12/1989 | Muller |
| 4,894,051 A | 1/1990 | Shiber |
| 4,911,148 A | 3/1990 | Sosnowski |
| 4,950,277 A | 8/1990 | Farr |
| 4,994,067 A | 2/1991 | Summers |
| 4,994,087 A | 2/1991 | Konrad et al. |
| 5,074,841 A | 12/1991 | Ademovic |
| 5,100,426 A | 3/1992 | Nixon |
| 5,114,399 A | 5/1992 | Kovalcheck |
| 5,122,134 A | 6/1992 | Borzone et al. |
| 5,231,989 A | 8/1993 | Middleman et al. |
| 5,242,461 A | 9/1993 | Kortenbach et al. |
| 5,267,955 A | 12/1993 | Hanson |
| 5,282,813 A | 2/1994 | Redha |
| 5,282,821 A | 2/1994 | Donahue |
| 5,284,128 A | 2/1994 | Hart |
| 5,304,189 A | 4/1994 | Goldberg et al. |
| 5,312,427 A | 5/1994 | Shturman |
| 5,314,438 A | 5/1994 | Shturman |
| 5,320,635 A | 6/1994 | Smith |
| 5,332,329 A | 7/1994 | Hill et al. |
| 5,334,211 A | 8/1994 | Shiber |
| 5,356,418 A | 10/1994 | Shturman |
| 5,358,472 A | 10/1994 | Vance et al. |
| 5,360,432 A | 11/1994 | Shturman |
| 5,370,609 A | 12/1994 | Drasler et al. |
| 5,372,587 A | 12/1994 | Hammerslag et al. |
| 5,409,454 A | 4/1995 | Fischell et al. |
| 5,417,703 A | 5/1995 | Brown et al. |
| 5,423,799 A | 6/1995 | Shiu |
| 5,429,604 A | 7/1995 | Hammersmark et al. |
| 5,429,617 A | 7/1995 | Hammersmark et al. |
| 5,431,173 A | 7/1995 | Chin et al. |
| 5,456,680 A | 10/1995 | Taylor et al. |
| 5,474,532 A | 12/1995 | Steppe |
| 3,358,472 A | 1/1996 | Klipping et al. |
| 5,489,291 A | 2/1996 | Wiley |
| 5,501,653 A | 3/1996 | Chin |
| 5,520,609 A | 5/1996 | Moll et al. |
| 5,529,580 A | 6/1996 | Kusunoki et al. |
| 5,540,706 A | 7/1996 | Aust |
| 5,554,163 A | 9/1996 | Shturman |
| 5,556,408 A | 9/1996 | Farhat |
| 5,569,197 A | 10/1996 | Helmus |
| 5,569,275 A | 10/1996 | Kotula |
| 5,584,843 A | 12/1996 | Wulfman |
| 5,618,294 A | 4/1997 | Aust |
| 5,626,562 A | 5/1997 | Castro |
| 5,632,755 A | 5/1997 | Nordgren |
| 5,634,178 A | 5/1997 | Sugiura |
| 5,634,883 A | 6/1997 | Chin |
| 5,643,178 A | 7/1997 | Moll |
| 5,643,251 A | 7/1997 | Hillsman |
| 5,643,297 A | 7/1997 | Nordgren |
| 5,643,298 A | 7/1997 | Nordgren |
| 5,649,941 A | 7/1997 | Lary |
| 5,656,562 A | 8/1997 | Wu |
| 5,665,062 A | 9/1997 | Houser |
| 5,665,098 A | 9/1997 | Kelly |
| 5,669,926 A | 9/1997 | Aust |
| 5,690,634 A | 11/1997 | Muller |
| 5,690,643 A | 11/1997 | Wijay |
| 5,695,506 A | 12/1997 | Pike |
| 5,716,327 A | 2/1998 | Warner |
| 5,725,543 A | 3/1998 | Redha |
| 5,728,129 A | 3/1998 | Summers |
| 5,733,297 A | 3/1998 | Wang |
| 5,743,456 A | 4/1998 | Jones |
| 5,746,758 A | 5/1998 | Nordgren |
| 5,749,885 A | 5/1998 | Sjostrom |
| 5,755,731 A | 5/1998 | Grinberg |
| 5,766,196 A | 6/1998 | Griffiths |
| 5,772,329 A | 6/1998 | Bardon |
| 5,779,721 A | 7/1998 | Nash |
| 5,782,834 A | 7/1998 | Lucey |
| 5,820,592 A | 10/1998 | Hammerslag |
| 5,826,582 A | 10/1998 | Sheehan |
| 5,828,582 A | 10/1998 | Conklen |
| 5,843,103 A | 12/1998 | Wulfman |
| 5,851,208 A | 12/1998 | Trott |
| 5,851,212 A | 12/1998 | Zirps |
| 5,865,082 A | 2/1999 | Cote |
| 5,865,098 A | 2/1999 | Anelli |
| 5,873,882 A | 2/1999 | Straub |
| 5,876,414 A | 3/1999 | Straub |
| 5,882,329 A | 3/1999 | Patterson |
| 5,882,333 A | 3/1999 | Schaer |
| 5,885,098 A | 3/1999 | Witkowski |
| 5,890,643 A | 4/1999 | Razon |
| 5,895,399 A | 4/1999 | Barbut |
| 5,895,508 A | 4/1999 | Halow |
| 5,897,566 A | 4/1999 | Shturman |
| 5,902,263 A | 5/1999 | Patterson |
| 5,902,283 A | 5/1999 | Darouiche |
| 5,902,313 A | 5/1999 | Redha |
| 5,910,150 A | 6/1999 | Saadat |
| 5,941,869 A | 8/1999 | Patterson |
| 5,941,893 A | 8/1999 | Saadat |
| 6,001,112 A | 12/1999 | Taylor |
| 6,015,420 A | 1/2000 | Gordon |
| 6,027,450 A | 2/2000 | Brown |
| 6,027,514 A | 2/2000 | Stine |
| 6,042,593 A | 3/2000 | Storz |
| 6,048,339 A | 4/2000 | Zirps |
| 6,053,923 A | 4/2000 | Veca |
| 6,066,153 A | 5/2000 | Lev |
| 6,080,170 A | 6/2000 | Nash |
| 6,086,153 A | 7/2000 | Heidmann |
| 6,090,118 A | 7/2000 | McGuckin |
| 6,113,615 A | 9/2000 | Wulfman |
| 6,132,444 A | 10/2000 | Shturman |
| 6,139,557 A | 10/2000 | Passafaro |
| 6,142,955 A | 11/2000 | Farascioni |
| 6,146,395 A | 11/2000 | Kanz |
| 6,152,938 A | 11/2000 | Curry |
| 6,156,046 A | 12/2000 | Passafaro |
| 6,165,209 A | 12/2000 | Patterson |
| 6,183,487 B1 | 2/2001 | Barry |
| 6,206,898 B1 | 3/2001 | Honeycutt |
| 6,237,405 B1 | 5/2001 | Leslie |
| 6,238,405 B1 | 5/2001 | Findlay |
| 6,241,744 B1 | 6/2001 | Imran |
| 6,258,098 B1 | 7/2001 | Taylor |
| 6,258,109 B1 | 7/2001 | Barry |
| 6,264,630 B1 | 7/2001 | Mickley |
| 6,284,830 B1 | 9/2001 | Gottschalk |
| 6,299,622 B1 | 10/2001 | Snow |
| 6,319,242 B1 | 11/2001 | Patterson |
| 6,355,027 B1 | 3/2002 | Le |

(56) References Cited

U.S. PATENT DOCUMENTS

| | | |
|---|---|---|
| 6,371,928 B1 | 4/2002 | Mcfann |
| 6,406,422 B1 | 6/2002 | Landesberg |
| 6,406,442 B1 | 6/2002 | Mcfann |
| 6,451,036 B1 | 9/2002 | Heitzmann |
| 6,454,779 B1 | 9/2002 | Taylor |
| 6,482,215 B1 | 11/2002 | Shiber |
| 6,482,217 B1 | 11/2002 | Pintor |
| 6,494,890 B1 | 12/2002 | Shturman |
| 6,497,711 B1 | 12/2002 | Plaia |
| 6,554,846 B2 | 4/2003 | Hamilton |
| 6,554,848 B2 | 4/2003 | Boylan |
| 6,562,049 B1 | 5/2003 | Norlander |
| 6,565,195 B2 | 5/2003 | Blair |
| 6,565,588 B1 | 5/2003 | Clement |
| 6,572,630 B1 | 6/2003 | McGucin |
| 6,578,851 B1 | 6/2003 | Bryant |
| 6,579,298 B1 | 6/2003 | Wyzgala |
| 6,579,299 B2 | 6/2003 | McGuckin |
| 6,596,005 B1 | 7/2003 | Kanz |
| 6,602,264 B1 | 8/2003 | McGuckin |
| 6,620,148 B1 | 9/2003 | Tsugita |
| 6,623,495 B2 | 9/2003 | Findlay |
| 6,629,953 B1 | 10/2003 | Boyd |
| 6,638,233 B2 | 10/2003 | Corvi |
| 6,638,288 B1 | 10/2003 | Shturman |
| RE38,335 E | 11/2003 | Aust |
| 6,656,195 B2 | 12/2003 | Peters |
| 6,658,195 B1 | 12/2003 | Senshu |
| 6,666,854 B1 | 12/2003 | Lange |
| 6,666,874 B2 | 12/2003 | Heitzmann |
| 6,682,545 B1 | 1/2004 | Kester |
| 6,702,830 B1 | 3/2004 | Demarais |
| 6,746,422 B1 | 6/2004 | Noriega |
| 6,758,851 B2 | 7/2004 | Shiber |
| 6,790,215 B2 | 9/2004 | Findlay |
| 6,800,085 B2 | 10/2004 | Selmon |
| 6,802,284 B2 | 10/2004 | Hironaka |
| 6,808,531 B2 | 10/2004 | Lafontaine |
| 6,818,001 B2 | 11/2004 | Wulfman et al. |
| 6,818,002 B2 | 11/2004 | Shiber |
| 6,830,577 B2 | 12/2004 | Nash |
| 6,843,797 B2 | 1/2005 | Nash |
| 6,860,235 B2 | 3/2005 | Anderson |
| 6,866,854 B1 | 3/2005 | Chang |
| 6,868,854 B2 | 3/2005 | Kempe |
| 6,876,414 B2 | 4/2005 | Hara |
| 6,936,056 B2 | 8/2005 | Nash |
| 6,991,409 B2 | 1/2006 | Noland et al. |
| 6,997,934 B2 | 2/2006 | Snow |
| 7,008,375 B2 | 3/2006 | Weisel |
| 7,025,751 B2 | 4/2006 | Silva |
| 7,033,357 B2 | 4/2006 | Baxter |
| 7,037,316 B2 | 5/2006 | McGuckin |
| RE39,152 E | 6/2006 | Aust |
| 7,172,610 B2 | 2/2007 | Heitzmann |
| 7,172,810 B2 | 2/2007 | Hashimoto |
| 7,235,088 B2 | 6/2007 | Pintor |
| 7,316,697 B2 | 1/2008 | Shiber |
| 7,344,546 B2 | 3/2008 | Wulfman |
| 7,344,548 B2 | 3/2008 | Toyota |
| 7,381,198 B2 | 6/2008 | Noriega |
| 7,399,307 B2 | 7/2008 | Evans |
| 7,479,147 B2 | 1/2009 | Honeycutt |
| 7,534,249 B2 | 5/2009 | Nash |
| 7,655,016 B2 | 2/2010 | Demarais |
| 7,666,161 B2 | 2/2010 | Nash |
| 7,734,332 B2 | 6/2010 | Sher |
| 7,771,445 B2 | 8/2010 | Heitzmann |
| 7,875,018 B2 | 1/2011 | Tockman |
| 7,879,022 B2 | 2/2011 | Bonnette |
| 7,892,230 B2 | 2/2011 | Woloszko |
| 7,981,128 B2 | 7/2011 | To |
| 8,007,500 B2 | 8/2011 | Lin |
| 8,007,506 B2 | 8/2011 | To |
| 8,015,420 B2 | 9/2011 | Cherian |
| 8,052,704 B2 | 11/2011 | Olson |
| 8,070,762 B2 | 12/2011 | Escudero et al. |
| 8,236,016 B2 | 8/2012 | To et al. |
| 8,337,516 B2 | 12/2012 | Escudero |
| 8,361,094 B2 | 1/2013 | To et al. |
| 8,469,979 B2 | 6/2013 | Olson |
| 8,517,994 B2 | 8/2013 | Li |
| 8,545,447 B2 | 10/2013 | Demarais |
| 8,568,432 B2 | 10/2013 | Straub |
| 8,572,630 B2 | 10/2013 | Woundy |
| 8,579,926 B2 | 11/2013 | Pintor |
| 8,585,726 B2 | 11/2013 | Yoon |
| 8,628,549 B2 | 1/2014 | To et al. |
| 8,632,560 B2 | 1/2014 | Pal et al. |
| 8,647,355 B2 | 2/2014 | Escudero |
| 8,747,350 B2 | 6/2014 | Chin |
| 8,795,306 B2 | 8/2014 | Smith et al. |
| 8,876,414 B2 | 11/2014 | Taniguchi |
| 8,881,849 B2 | 11/2014 | Shen et al. |
| 8,888,801 B2 | 11/2014 | To et al. |
| 8,932,208 B2 | 1/2015 | Kendale et al. |
| 9,050,127 B2 | 6/2015 | Bonnette et al. |
| 9,095,371 B2 | 8/2015 | Escudero et al. |
| 9,198,679 B2 | 12/2015 | To et al. |
| 9,220,530 B2 | 12/2015 | Moberg |
| 9,498,247 B2 | 3/2016 | Patel et al. |
| 9,308,016 B2 | 4/2016 | Escudero et al. |
| 9,314,263 B2 | 4/2016 | Escudero et al. |
| 9,345,511 B2 | 5/2016 | Smith |
| 9,498,600 B2 | 11/2016 | Rosenthal et al. |
| 9,604,291 B2 | 3/2017 | Kountanya et al. |
| 9,675,376 B2 | 6/2017 | To et al. |
| 9,717,520 B2 | 8/2017 | Zeroni et al. |
| 9,770,258 B2 | 9/2017 | Smith et al. |
| 9,883,873 B2 | 2/2018 | Kulas et al. |
| 9,968,371 B2 | 5/2018 | Todd et al. |
| 9,976,356 B2 | 5/2018 | Burhan et al. |
| 10,022,145 B2 | 7/2018 | Simpson et al. |
| 10,028,767 B2 | 7/2018 | Germain et al. |
| 10,154,854 B2 | 12/2018 | To et al. |
| 10,251,667 B2 | 4/2019 | Cohen et al. |
| 10,349,974 B2 | 7/2019 | Patel et al. |
| 10,441,311 B2 | 10/2019 | Smith et al. |
| 10,507,036 B2 | 12/2019 | Schuman et al. |
| 10,524,824 B2 | 1/2020 | Rottenberg et al. |
| 10,555,753 B2 | 2/2020 | Moberg et al. |
| 10,568,655 B2 | 2/2020 | Simpson et al. |
| 10,774,596 B2 | 9/2020 | Zhang et al. |
| 11,304,723 B1 | 4/2022 | To et al. |
| 11,317,940 B2 | 5/2022 | Smith et al. |
| 2001/0005909 A | 1/2001 | Findlay |
| 2001/0004700 A1 | 6/2001 | Honeycutt |
| 2002/0004680 A1 | 1/2002 | Plaia |
| 2002/0007190 A1 | 1/2002 | Wulfman |
| 2002/0198550 A1 | 1/2002 | Nash |
| 2002/0029057 A1 | 3/2002 | McGuckin |
| 2002/0169487 A1 | 3/2002 | Graindorge |
| 2002/0077642 A1 | 6/2002 | Patel |
| 2002/0077842 A1 | 6/2002 | Charisius |
| 2002/0168467 A1 | 7/2002 | Puech |
| 2002/0107479 A1 | 8/2002 | Bates |
| 2002/0151918 A1 | 10/2002 | Lafontaine |
| 2002/0169467 A1 | 11/2002 | Heitzmann |
| 2003/0018346 A1 | 1/2003 | Follmer |
| 2003/0078606 A1 | 4/2003 | Lafontaine |
| 2003/0100911 A1 | 5/2003 | Nash |
| 2003/0114869 A1 | 6/2003 | Nash |
| 2003/0125758 A1 | 7/2003 | Simpson |
| 2003/0139751 A1 | 7/2003 | Evans |
| 2003/0139802 A1 | 7/2003 | Wulfman |
| 2004/0006358 A1 | 1/2004 | Wulfman |
| 2004/0181249 A1 | 1/2004 | Torrance |
| 2004/0199051 A1 | 3/2004 | Weisel |
| 2004/0220519 A1 | 3/2004 | Wulfman |
| 2004/0230212 A1 | 3/2004 | Wulfman |
| 2004/0230213 A1 | 3/2004 | Wulfman |
| 2004/0235611 A1 | 3/2004 | Nistal |
| 2004/0236312 A1 | 3/2004 | Nistal |
| 2004/0238312 A1 | 3/2004 | Sudau |

(56) References Cited

U.S. PATENT DOCUMENTS

| | | |
|---|---|---|
| 2004/0243162 A1 | 3/2004 | Wulfman |
| 2004/0202772 A1 | 4/2004 | Matsuda |
| 2004/0087988 A1 | 5/2004 | Heitzmann |
| 2004/0097995 A1 | 5/2004 | Nash |
| 2004/0102772 A1 | 5/2004 | Baxter |
| 2004/0103516 A1 | 6/2004 | Bolduc |
| 2004/0147934 A1 | 7/2004 | Kiester |
| 2004/0167533 A1 | 8/2004 | Wilson |
| 2004/0167553 A1 | 8/2004 | Simpson |
| 2004/0167554 A1 | 8/2004 | Simpson |
| 2005/0004585 A1 | 1/2005 | Hall |
| 2005/0020327 A1 | 1/2005 | Chung |
| 2005/0020974 A1 | 1/2005 | Noriega |
| 2005/0059990 A1 | 3/2005 | Ayala |
| 2005/0149084 A1 | 3/2005 | Kanz |
| 2005/0222519 A1 | 4/2005 | Simpson |
| 2005/0113853 A1 | 5/2005 | Noriega |
| 2005/0177068 A1 | 8/2005 | Simpson |
| 2005/0197661 A1 | 9/2005 | Carrison et al. |
| 2005/0197861 A1 | 9/2005 | Omori |
| 2005/0240146 A1 | 10/2005 | Nash |
| 2006/0020327 A1 | 1/2006 | Lashinski |
| 2006/0239982 A1 | 1/2006 | Simpson |
| 2006/0074442 A1 | 4/2006 | Noriega |
| 2006/0241564 A1 | 4/2006 | Corcoran |
| 2006/0229646 A1 | 10/2006 | Sparks |
| 2007/0225739 A1 | 5/2007 | Pintor |
| 2007/0282303 A1 | 5/2007 | Nash |
| 2007/0135733 A1 | 6/2007 | Soukup |
| 2007/0282350 A1 | 6/2007 | Hernest |
| 2007/0250000 A1 | 10/2007 | Magnin |
| 2007/0282358 A1 | 12/2007 | Remiszewski |
| 2008/0004643 A1 | 1/2008 | To |
| 2008/0004644 A1 | 1/2008 | To |
| 2008/0004645 A1 | 1/2008 | To |
| 2008/0004647 A1 | 1/2008 | To |
| 2008/0045986 A1 | 2/2008 | To |
| 2008/0234715 A1 | 3/2008 | Pesce |
| 2008/0249364 A1 | 4/2008 | Korner |
| 2008/0103516 A1 | 5/2008 | Wulfman |
| 2008/0140101 A1 | 6/2008 | Carley |
| 2008/0004646 A1 | 10/2008 | To |
| 2009/0018565 A1 | 1/2009 | To et al. |
| 2009/0018566 A1 | 1/2009 | Escudero |
| 2009/0018567 A1 | 1/2009 | Escudero |
| 2009/0024085 A1 | 1/2009 | To |
| 2009/0234378 A1 | 9/2009 | Escudero |
| 2010/0010492 A1 | 1/2010 | Lockard |
| 2010/0049225 A1 | 2/2010 | To |
| 2010/0324567 A1 | 6/2010 | Root |
| 2010/0174302 A1 | 7/2010 | Heitzmann |
| 2010/0324576 A1 | 8/2010 | Pintor |
| 2011/0040315 A1 | 2/2011 | To |
| 2011/0152906 A1 | 2/2011 | Escudero |
| 2011/0152907 A1 | 2/2011 | Escudero |
| 2011/0112563 A1 | 5/2011 | To |
| 2011/0270289 A1 | 7/2011 | To |
| 2011/0301626 A1 | 8/2011 | To |
| 2012/0083810 A1 | 4/2012 | Escudero |
| 2013/0158578 A1 | 3/2013 | Ghodke |
| 2013/0085515 A1 | 4/2013 | To |
| 2013/0090674 A1 | 4/2013 | Escudero |
| 2013/0096587 A1 | 4/2013 | Smith |
| 2013/0103062 A1 | 4/2013 | To |
| 2013/0103063 A1 | 4/2013 | Escudero |
| 2013/0296901 A1 | 11/2013 | Olson |
| 2014/0039532 A1 | 2/2014 | Vrba |
| 2014/0058423 A1 | 2/2014 | Smith |
| 2014/0107680 A1 | 4/2014 | Escudero |
| 2015/0224585 A1 | 1/2015 | Kuroda |
| 2016/0183966 A1* | 6/2016 | McGuckin, Jr. ............ A61B 17/320758 606/159 |
| 2017/0273698 A1 | 2/2017 | McGuckin et al. |
| 2018/0193056 A1 | 7/2018 | Colyer et al. |
| 2020/0029801 A1 | 1/2020 | Tachibana et al. |
| 2020/0029998 A1 | 1/2020 | Ogle et al. |
| 2020/0060718 A1 | 2/2020 | Patel et al. |
| 2020/0129202 A1 | 4/2020 | Schoenle et al. |
| 2020/0315654 A1 | 10/2020 | Patel et al. |
| 2020/0352552 A1 | 11/2020 | Rousso et al. |
| 2022/0387071 A1 | 6/2022 | To et al. |

FOREIGN PATENT DOCUMENTS

| | | |
|---|---|---|
| EP | 0817595 | 3/1996 |
| EP | 0950456 A1 | 10/1999 |
| EP | 1158910 | 1/2000 |
| EP | 1176915 | 2/2002 |
| EP | 1178315 | 2/2002 |
| EP | 1315460 | 6/2003 |
| EP | 1603486 B1 | 6/2006 |
| EP | 1722694 | 11/2006 |
| EP | 1870044 | 12/2007 |
| EP | 1617893 A4 | 8/2008 |
| EP | 2579791 B1 | 6/2010 |
| EP | 2462881 | 6/2012 |
| EP | 2617372 B1 | 7/2013 |
| EP | 2641551 | 9/2013 |
| EP | 2424608 B1 | 3/2014 |
| EP | 2211732 B1 | 5/2018 |
| EP | 2164409 B1 | 8/2018 |
| EP | 3027126 B1 | 10/2019 |
| EP | 2931151 B1 | 11/2019 |
| JP | 2006511256 | 4/2006 |
| JP | 2011136180 A | 7/2011 |
| JP | 2013531542 A | 8/2013 |
| JP | 6266108 B2 | 1/2018 |
| JP | 6356604 B2 | 7/2018 |
| WO | WO 1992/001423 | 2/1992 |
| WO | WO 1992/014506 | 9/1992 |
| WO | WO 1994/024946 | 11/1994 |
| WO | WO 1995/021576 | 8/1995 |
| WO | WO 1996/029941 | 10/1996 |
| WO | WO 1996/029942 | 10/1996 |
| WO | WO 1999/023958 | 5/1999 |
| WO | WO 1999/035977 | 7/1999 |
| WO | WO 2000/054659 | 9/2000 |
| WO | WO 2000/054859 | 9/2000 |
| WO | WO 2001/064115 | 9/2001 |
| WO | WO 2001/074255 | 10/2001 |
| WO | WO 2001/076680 | 10/2001 |
| WO | WO 2005/084562 | 9/2005 |
| WO | WO 2005/123169 | 12/2005 |
| WO | WO 2006/028886 | 3/2006 |
| WO | WO 2007/010389 | 1/2007 |
| WO | WO 2008/005888 | 1/2008 |
| WO | WO 2008/005891 | 1/2008 |
| WO | WO 2009/005779 | 1/2009 |
| WO | WO 2009/054968 | 4/2009 |
| WO | WO 2009/126309 | 10/2009 |
| WO | WO 2010/050391 | 5/2010 |
| WO | WO 2013/056262 | 4/2013 |
| WO | WO 2013/172970 | 11/2013 |
| WO | WO 2015/017114 | 2/2015 |
| WO | WO 2020/234203 | 11/2020 |

OTHER PUBLICATIONS

U.S. Appl. No. 63/197,970 (priority for U.S. Appl. No. 17/518,294, cited herein), To, et al.—owned by Applicant, filed Jun. 7, 2021.

PCT/US22/32428 Published as WO 2022/261043, To—owned by Applicant, Jun. 7, 2022.

Written opinion and search report for PCT/US22/32428, To—owned by Applicant, Jun. 7, 2022.

Ikeno et al. Initial Experience with the Novel 6 F r-Compatible System for Debulking De Novo Coronary Arterial Lesions. Catheterization and Cardiovascular Interventions 62:308-17. (2004).

Kanjwal et al. Peripheral Arterial Disease—A Silent Killer. JK-Practitioner 11(4):225-32 (2004).

(56) References Cited

OTHER PUBLICATIONS

Nakamura et al. Efficacy and Feasibility of Helixcision for Debulking Neointimal Hyperplasia for In-Stent Restenosis. Catheterization and Cardiovascular Interventions 57:460-66 (2002).

* cited by examiner

PRIOR ART

TELESCOPING ATHERECTOMY DEVICE

CROSS REFERENCES TO RELATED APPLICATIONS

This is a continuation application of U.S. application Ser. No. 17/518,294, filed Nov. 3, 2021, which claims priority to U.S. Provisional Application Nos. 63/126,847, filed Dec. 17, 2020, and 63/197,970, filed Jun. 7, 2021, each of which is hereby incorporated herein by reference in its entirety.

BACKGROUND

Field of the Invention

The teachings herein are directed generally to medical devices and methods, including devices and methods for performing atherectomies.

Description of the Related Art

An atherectomy is a minimally invasive procedure for removing atherosclerosis from blood vessels within the body and is an alternative to angioplasty in the treatment of narrowing arteries. Common applications include peripheral arterial disease and coronary artery disease. Unlike angioplasty and stents, which push plaque into the vessel wall, the atherectomy procedure cuts plaque away from the wall of a blood vessel. While atherectomies are usually used to remove plaque from arteries, they can also be used in veins and vascular bypass grafts, for example.

Atherectomies can offer improvements over balloon dilatation and stent placement, which are considered traditional interventional surgical methods of treating atherosclerosis. In balloon dilatation, a collapsed balloon is inserted into a blood vessel and inflated to push plaque against the vessel wall, and the stent can be placed to hold the plaque as a scaffolding in order to try and maintain the integrity of the lumen of the vessel. However, such traditional treatments can stretch the artery and induce scar tissue formation, while the placement of a stent may also cut arterial tissue and induce scar tissue formation. The scar tissue formation can lead to restenosis of the artery. Moreover, the dilatation with the balloon can also rip the vessel wall. Because atherectomies enlarge the lumen by removing plaque rather than stretching the vessel, risk of suffering vessel injuries, such as dissections that can lead to increased restenosis, is reduced.

Unfortunately, the art suffers performance limitations in state-of-the-art atherectomy devices. For example, current devices with rotating cutters cannot handle the variety of soft, fibrous and calcific plaque effectively, either not cutting all types of plaque or breaking up the plaque into large pieces that remain in the arterial bed as emboli that can clog blood vessels downstream. As plaque is a tissue made of fat, cholesterol, calcium, fibrous connective tissue and other substances found in the body, it can be highly variable and classified mainly into four different types of tissue: calcified and hard, necrotic and soft, fibrotic, and a combination thereof. Calcified plaque can be hard as a bone; fatty plaque is typically soft; and fibrotic plaque is typically viscoelastic, stretchy yet firm, and thus difficult to cut. Some state-of-the-art devices have burrs that can grind-away hard plaque but can't cut soft or viscoelastic plaque. Worse yet, they can loosen debris that can become dangerous emboli. Some state-of-the-art devices have a sharp cutter that can be deflected against one side of the vessel to do eccentric cutting, which is desirable, but the amount of deflection can't be effectively controlled. And, some state-of-the-art devices have a "nose cone" that prevents the cutter from cutting through lesion that doesn't allow enough progression of the device to reach the cutter blades.

Most importantly, however, is that patients having "tight" or "tough" lesions are currently unable to receive treatments with balloons, stents, or atherectomy devices. Such lesions are occlusions that leave only a very small luminal opening, or no opening, making it difficult-to-impossible to achieve passage of a guidewire, much less passage of a balloon or stent on the guidewire. For example, a luminal opening that is only 0.5 mm may allow passage of a guidewire, perhaps, but the smallest stents may be 1.0 mm, and the smallest balloon may be 0.75 mm, neither of which can pass through a tough, small lesion for the treatment. And, as noted above, current atherectomy devices have a difficult time cutting away the plaque, even if the guidewire might be able to pass through the luminal opening. In situations having a total occlusion, the problem is exacerbated.

As such, one of skill will appreciate an atherectomy device that (i) can effectively cut and remove the 4 different types of plaque tissue, namely calcified and hard, necrotic and soft, fibrotic, and a combination thereof; (ii) can render a concentric vessel lumen with minimal plaque burden; (iii) can safely self-collect and remove plaque particles to avoid release of emboli; and, (iv) can effectively treat a blood vessel with a reduced risk of suffering vessel injuries that can lead to increased restenosis. In addition, the skilled artisan will certainly appreciate having an atherectomy device that (v) can handle these tight or tough lesions.

SUMMARY

Atherectomy devices, and methods of using them are provided, namely devices and methods that (i) can effectively cut and remove the 4 different types of plaque tissue, namely calcified and hard, necrotic and soft, fibrotic, and a combination thereof; (ii) can render a concentric vessel lumen with minimal plaque burden; (iii) can safely self-collect and remove plaque particles to avoid release of emboli; (iv) can effectively treat a blood vessel with a reduced risk of suffering vessel injuries that can lead to increased restenosis; and, importantly, (v) can also handle tight or tough lesions having little to no luminal opening in the lesion. The atherectomy devices taught herein can be telescoping, self-driving, lateral pushing, or a combination thereof.

In some embodiments, the atherectomy device is a telescoping atherectomy device. In these embodiments, the device can have a distal end, a proximal end, a long axis, and a guidewire lumen passing through the device in the direction of the long axis. The device can include a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, in these embodiments, the cleared diameter of the cutter can be greater than the outer diameter of the flexible drive shaft; the flexible drive shaft can be longer than the flexible sheath to enable a reversible telescoping of the drive assembly from the lumen of the flexible sheath at the distal end of the flexible sheath; and, the guidewire lumen can include the cutter lumen and the driveshaft lumen.

In some embodiments, the cleared diameter of the cutter can be greater than the outer diameter of the flexible sheath. And, in some embodiments, the positive displacement pump can be a screw pump attached to the outer surface of the drive shaft, the distal end of the screw pump being adjacent to the helical flutes at the proximal end of the cutter.

In some embodiments, the telescoping atherectomy device can be self-driving. For example, the screw pump can extend beyond the flexible sheath and can be exposed for contact with a vascular lumen during use of the atherectomy device within the vascular lumen. In some embodiments, the screw pump can be a right hand screw when the cutter is rotated in the right-hand direction; and, in some embodiments, the screw pump can be a left hand screw when the cutter is rotated in the left-hand direction.

In some embodiments, the telescoping atherectomy device can further comprise a reversibly-expandable, lateral pushing member at the distal end of the flexible sheath. In some embodiments, the telescoping atherectomy device can further comprise a reversibly-expandable, lateral pushing member at the distal end of the flexible sheath, the lateral pushing member having a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, the operable connection with the cutter can be configured as a rotatably translatable connection to facilitate a rotation of the cutter and the flexible drive shaft without rotating the lateral pushing member during operation of the atherectomy device.

In some embodiments, the atherectomy device is a self-driving atherectomy device. In these embodiments, the device can have a distal end, a proximal end, a long axis, and a guidewire lumen passing through the device in the direction of the long axis. The device can include a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a screw pump attached to the outer surface of the drive shaft and adjacent to the helical flutes at the proximal end of the cutter, the screw pump including a drive screw portion. In some embodiments, the drive screw portion can extend beyond the flexible sheath and can be exposed for contact with a vascular lumen during use of the atherectomy device within the vascular lumen. In some embodiments, the drive screw portion can be a right hand screw when the cutter is rotated in the right-hand direction; and, in some embodiments, the drive screw portion can be a left hand screw when the cutter is rotated in the left-hand direction. And, in these embodiments, the cleared diameter of the cutter can be greater than the outer diameter of the flexible drive shaft; and, the guidewire lumen can include the cutter lumen and the driveshaft lumen.

In some embodiments, the cleared diameter of the cutter of the self-driving atherectomy device can be greater than the outer diameter of the flexible sheath. And, in some embodiments, the drive screw portion can be the distal portion of the screw pump.

In some embodiments, the flexible drive shaft of the self-driving atherectomy device can be longer than the flexible sheath to enable a reversible telescoping of the drive assembly from the lumen of the flexible sheath at the distal end of the flexible sheath.

In some embodiments, the self-driving atherectomy device can further comprise a reversibly-expandable, lateral pushing member at the distal end of the flexible sheath. In some embodiments, the lateral pushing member can have a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, in some embodiments, the operable connection with the cutter can be configured as a rotatably translatable connection to facilitate a rotation of the cutter and the flexible drive shaft without rotating the lateral pushing member during operation of the atherectomy device.

In some embodiments, the atherectomy device is a lateral pushing atherectomy device. In these embodiments, the device can have a distal end, a proximal end, a long axis, and a guidewire lumen passing through the device in the direction of the long axis. The device can include a flexible sheath having an outer diameter and a sheath lumen. a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, the lateral pushing atherectomy device can also have a reversibly-expandable, lateral pushing member at the distal end of the flexible sheath. In these embodiments, the cleared diameter of the cutter can be greater than the outer diameter of the flexible drive shaft; and, the guidewire lumen can include the cutter lumen and the driveshaft lumen.

In some embodiments, the cleared diameter of the cutter can be greater than the outer diameter of the flexible sheath.

In some embodiments, the lateral pushing member can have a proximal end, a distal end, a collapsed state, and an expanded state, the proximal end having an operable connection with the flexible sheath, and the distal end having an operable connection with the cutter. In some embodiments, the operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. And, in some embodiments, the operable connection with the cutter can be configured as a rotatably translatable connection to facilitate a rotation of the cutter and the flexible drive shaft without rotating the lateral pushing member during operation of the atherectomy device.

In some embodiments, the flexible drive shaft of the laterally pushing atherectomy device can be longer than the flexible sheath to enable a reversible telescoping of the drive assembly from the lumen of the flexible sheath at the distal end of the flexible sheath. And, in some embodiments, the laterally pushing atherectomy device can comprise a drive screw attached to the outer surface of the distal end of the drive shaft and adjacent to the screw pump at the distal end of the screw pump. The drive screw can extend beyond the flexible sheath and can be exposed for contact with a vascular lumen during use of the atherectomy device within the vascular lumen. In some embodiments, the drive screw can be a right hand screw when the cutter is rotated in the right-hand direction; and, in some embodiments, the drive screw can be a left hand screw when the cutter is rotated in the left-hand direction.

Systems are also provided. In some embodiments, any of the atherectomy devices taught herein can be a system comprising the atherectomy device and a guidewire.

Methods of performing an atherectomy in a subject using any of the atherectomy devices taught herein are provided. In some embodiments, the methods can include creating a point of entry in a vascular lumen of the subject; inserting the atherectomy device into the vascular lumen; telescoping the flexible drive shaft; cutting a plaque from the vascular lumen with the cutter of the atherectomy device; discharging the cut plaque from the vascular lumen with the positive displacement pump; and, removing the atherectomy device from the vascular lumen of the subject.

In some embodiments, the methods can include creating a point of entry in a vascular lumen of the subject; inserting the atherectomy device into the vascular lumen; driving the atherectomy device through the vascular lumen with the exposed drive screw; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include creating a point of entry in a vascular lumen of the subject; inserting the atherectomy device into the vascular lumen; pushing the distal portion of the atherectomy device laterally in the vascular lumen, the pushing including expanding the lateral pushing member; cutting a plaque from the vascular lumen with the cutter of the atherectomy device; discharging the cut plaque from the vascular lumen with the positive displacement pump; and, removing the atherectomy device from the vascular lumen of the subject.

DETAILED DESCRIPTION

Atherectomy devices, and methods of using them are provided, namely devices and methods that (i) can effectively cut and remove the 4 different types of plaque tissue, namely calcified and hard, necrotic and soft, fibrotic, and a combination thereof, including fibrocalcific tissue; (ii) can render a concentric vessel lumen with minimal plaque burden; (iii) can safely self-collect and remove plaque particles to avoid release of emboli; (iv) can effectively treat a blood vessel with a reduced risk of suffering vessel injuries that can lead to increased restenosis. And, importantly, one of skill will certainly appreciate an atherectomy device that, surprisingly, (v) can also handle tight or tough lesions having little to no luminal opening in the lesion. The atherectomy devices taught herein can be telescoping, self-driving, lateral pushing, or a combination thereof. The devices provided herein can, for example, render a concentric lumen with minimal plaque burden (<30% vessel diameter) while avoiding damage to vessel wall and minimizing embolization.

Figure 1A:
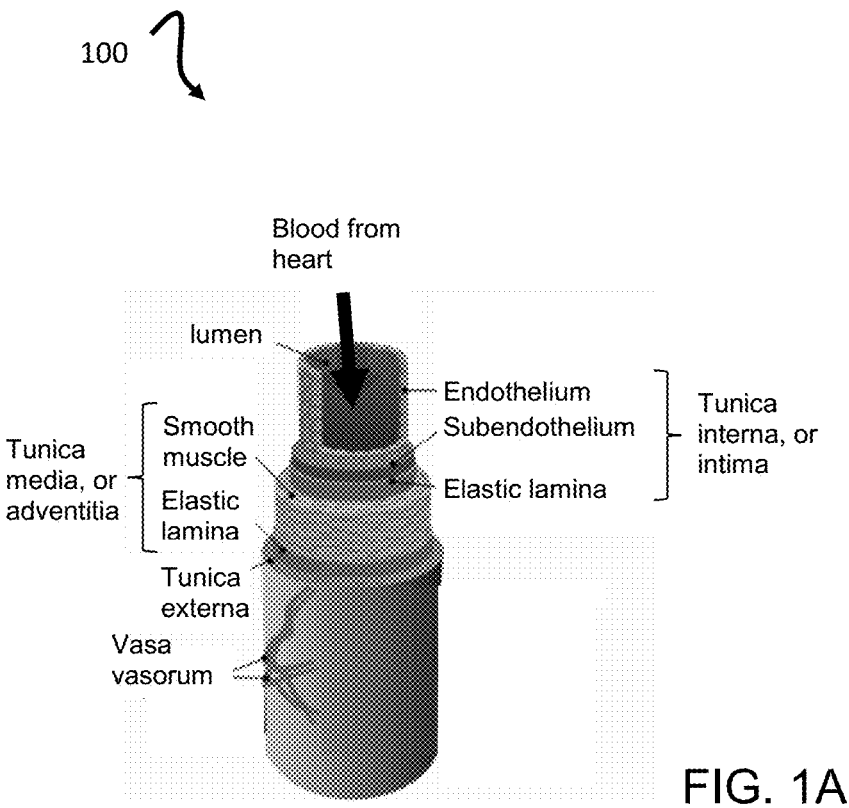
FIGS. 1A-1C illustrate the anatomy of an artery, intimal plaque, and a method of plaque removal, according to some embodiments.
Figure 1B:
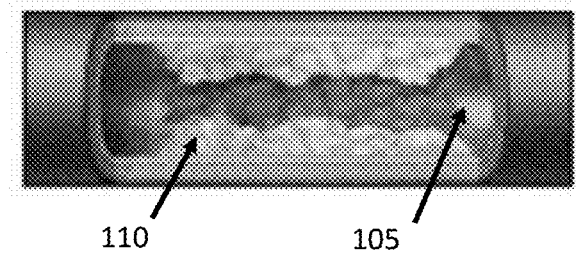
Figure 1C:
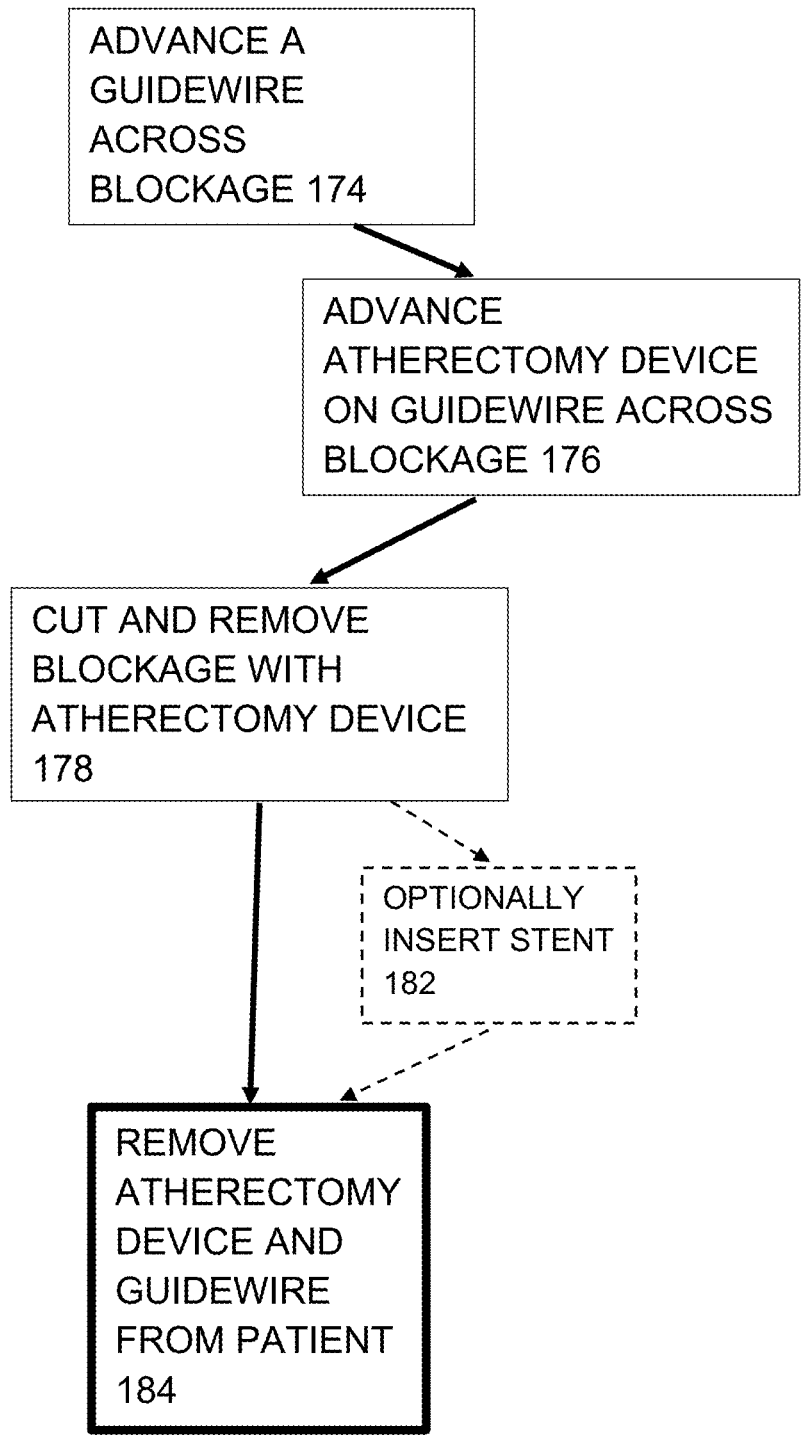

FIGS. 1A-1C illustrate the anatomy of an artery, intimal plaque, and a method of plaque removal, according to some embodiments. FIG. 1A illustrates the anatomy of an artery 100. The anatomy of arteries can vary by size of the artery, but arteries share common characteristics. They transport oxygenated blood from the heart and to smaller arterioles. The outermost layer is the tunica externa, or tunica adventitia, and is composed of collagen fibers. The largest arteries, like the aorta, also have vasa vasorum, or small blood vessels that supply oxygen to the large blood vessels. The next layer in is the tunica media, which is a combination of smooth muscle, collagen fiber, and is elastic. The next layer is the tunica interna or intima, which is also elastic with endothelial cells supported by a layer of collagen. These layers all surround the vascular lumen, which is the wall upon which the undesirable plaque forms and is removed with the atherectomy devices taught herein. FIG. 1B illustrates plaque 110 that has deposited on the wall of the arterial lumen 105.

Those of skill understand that guidewires can be used to locate a diseased region, or target region, in a blood vessel. Also, a guidewire can be used to direct the atherectomy devices taught herein, namely the cutter, over the target region. In some embodiments, the guidewire lumen can include the cutter lumen and the driveshaft lumen. In some embodiments, the guidewire lumen diameter can range in size from 0.01 to 0.20 inches, from 0.01 to 0.18 inches, from 0.01 to 0.15 inches, from 0.01 to 0.10 inches, or any range therein in some embodiments. In some embodiments, the guidewire lumen diameter can range from 0.01 to 0.14 inches. In some embodiments, the guidewire lumen diameter is 0.01 inches (0.254 mm), 0.02 inches (0.508 mm), 0.04 inches (1.016 mm), 0.06 inches (1.524 mm), 0.08 inches (2.032 mm), 0.10 inches (2.540 mm), 0.12 inches (3.048 mm), 0.14 inches (3.556 mm), 0.16 inches (4.064 mm), 0.18 inches (4.572 mm), 0.20 inches (5.080 mm), or any diameter therein in increments of 0.01 inches (0,254 mm).

FIG. 10 is a flowchart of an atherectomy method 150 that can be used with the atherectomy devices taught herein to remove plaque from an artery. A guidewire is advanced 174 through a guiding catheter and across a blockage in the blood vessel created by the arterial plaque in the target area. Once the guidewire is in place across the blockage, an atherectomy device is advanced 176 across the blockage on the guidewire. The atherectomy device is then in proper position to cut and remove 178 plaque in the target area to treat the artery and remove the blockage. At this time, a stent can optionally be inserted 180 in the target area to help maintain the newly created opening in the lumen. To complete the procedure, the atherectomy device and guidewire are removed 182 from the patient.

Generally speaking the atherectomy devices can include a cutter, or cutting head, that is attached to a drive shaft that rotates the cutter, and the drive shaft rotates within a sheath. The sheath can be interchangeably called a "flexible tube", in some embodiments; and, the drive shaft can be referred to as a "torque shaft", in some embodiments. In some embodiments, the cutter can be designed to telescope from the sheath and, in some embodiments, reversibly telescope from the sheath. In some embodiments, the cutter can extend out, or telescope, from the sheath as far as desired. For example, the cutter can telescope from, perhaps, 10 mm to 500 mm from the end of the sheath on the drive shaft in some embodiments. The telescoping allows the cutter and the distal portion of the drive shaft to advance ahead of the sheath during which an improved engagement between the cutter and the plaque tissue can be achieved. In addition, leaving the sheath static while moving the cutter in advance of the sheath allows the sheath to resist drill through. In some methods, the telescoping can be the sole step in the removal of plaque from a vessel. In some embodiments, the telescoping can provide an initial cutting path to facilitate a subsequent and more target-specific eccentric cutting.

Figure 2A:
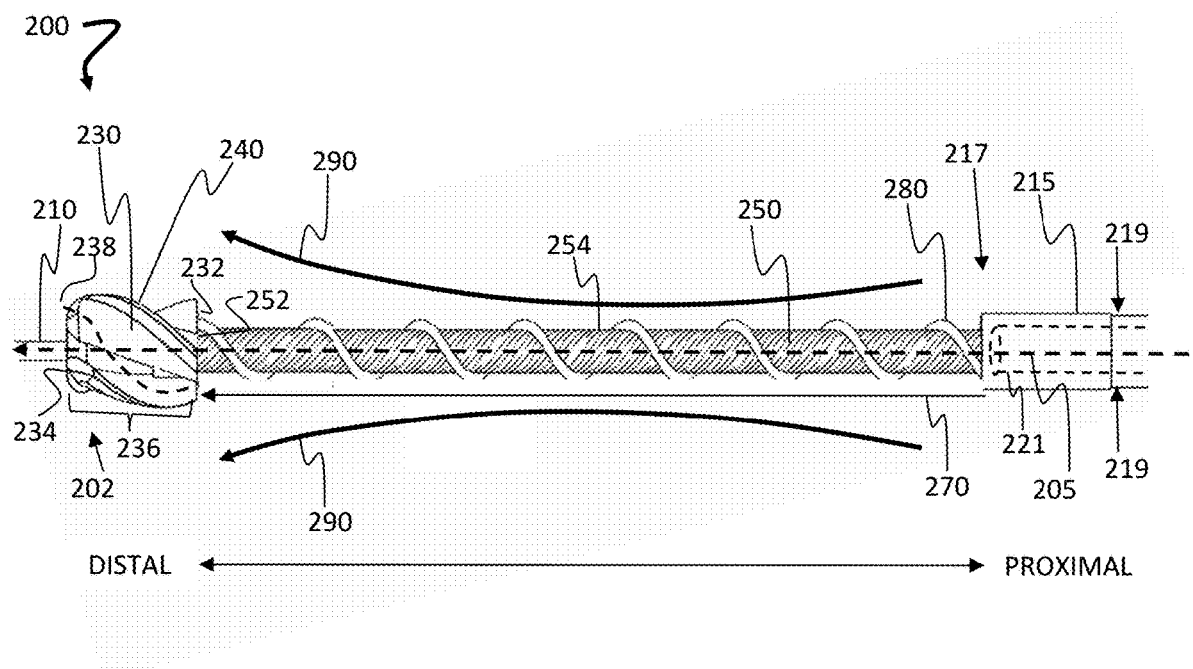
FIGS. 2A and 2B illustrate a telescoping atherectomy device, according to some embodiments.
Figure 2B:
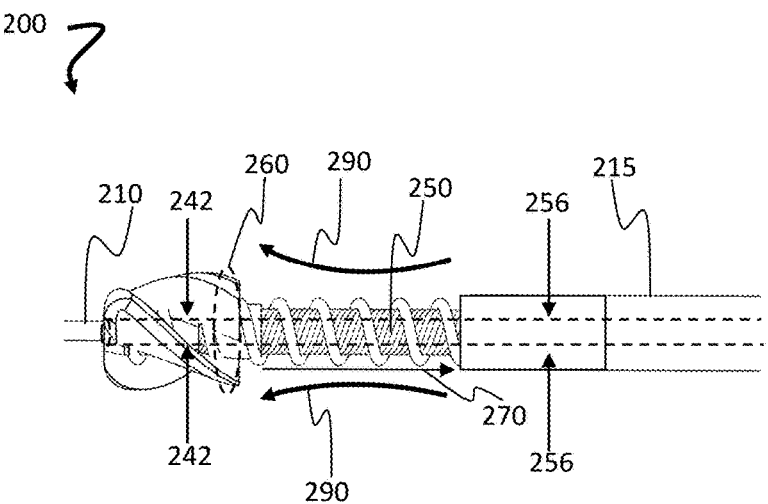

FIGS. 2A and 2B illustrate a telescoping atherectomy device, according to some embodiments. In these embodiments, the atherectomy device 200 can have a distal portion with a distal end 202, a proximal portion with a proximal end (not shown), a long axis having a central axis 205, and a guidewire lumen passing through the device in the direction of the central axis 205 for a guidewire 210. For perspective, the general direction of orientation from proximal to distal, and distal to proximal, are illustrated in FIG. 2A. The device can include a flexible sheath 215 having a proximal portion with a proximal end (not shown), a distal portion with a distal end 217, an outer diameter 219, and a sheath lumen 221; a drive shaft 250; a cutter 230 having a proximal portion with a proximal end 232, a distal portion with a distal end 234, and a body 236 with a plurality of helical flutes 238 between the cutter blades 240. The distal end 234 can have a plurality of cutting lips on the cutter blades 240, and, in some embodiments, the distal end 234 can have a point. The cutter can have a cutter lumen 242, and a cleared diameter 260.

The drive shaft can be made using any construct known to one of skill that meets the axial stiffness, flexural stiffness, torsional stiffness, and the like. In some embodiments, for example, the drive shaft includes a distal end and a proximal end, in which the distal end connects to or affixed to the cutter, and the proximal end connected to a rotatable element such as a gear attached to a motor or attached to motor itself. The drive shaft may be, in turn, driven by the motor in the handle. The drive shaft can be made using a metal braid and/or one or more metal coils, and one or more portions of the drive shaft embedded in a polymer. In some embodiments, the polymer can include PEBAX, polyurethane, polyethylene, fluoropolymers, parylene, polyimide, PEEK, PET, or a combination thereof. In some variations, the drive shaft can include a rigid material such as plastic, rendered flexible by incorporation of a spiral relief or groove. During a procedure, the motor drives the gear to rotate drive shaft and cutter to cut the tissue in a target lesion.

One of skill will appreciate that the "cleared diameter" of a vessel can be used to describe the diameter of the lumen of the blood vessel after passage of the cutter portion of the atherectomy device through the lumen of the vessel. Since the vessel is often elastic, the cleared diameter 260 of the lumen of a blood vessel may or may not be equal to the diameter of the cutter 230. The cleared diameter 260 of the cutter 230 can be greater than the outer diameter of the flexible drive shaft 250. In some embodiments, the cleared diameter of the cutter can be greater than the outer diameter of the flexible sheath. And, in some embodiments, the cleared diameter 260 of the lumen is less than the diameter of the body of the cutter 230.

Table 1 lists example arterial lumen diameters in mm, beginning at the aorta and descending down a human leg, for example. Peripheral vascular disease in the legs is an example of a condition that can be treated using the atherectomy devices taught herein.

TABLE 1

Examples of arterial lumen diameters in mm.

| Aorta (mm) | Superior femoral artery (mm) | Popliteal artery (mm) | Anterior tibial artery (mm) | Tibio-peroneal trunk (mm) | Posterior tibial arteries (mm) | Peroneal arteries (mm) |
|---|---|---|---|---|---|---|
| 17-35 | 5-7 | 3.5-4.5 | 3.0 | 2.5 | 2.0 | 2.0 | the superior femoral artery, located about mid-femur, generally has a diameter of about 5 to 7 mm, or about 0.2 to 0.25 inch. As the artery descends below the knee, the popliteal artery generally has a diameter of about 4 to 4.5 mm (0.157 inch to 0.177 inch), and then reduces to about 3.5 mm (0.137 inch) as you move in the direct of the subject's foot. The popliteal artery branches again into the anterior tibial artery and the tibioperoneal trunk, reducing further in diameter to about 3.0 mm and then about 2.5 mm or about 0.118 inch to 0.098 inch. The tibioperoneal trunk further subdivides into the posterior tibial and peroneal arteries, further reducing in diameter to about 2.0 mm (0.078 inch). Generally speaking, the diameters of the peripheral arteries of the leg can vary, typically, from about 2 mm to about 7 mm. Any blood vessel can contain plaque and be a prospective target area for the atherectomy devices taught herein. For example, coronary arteries are about 3 mm in size, varies from 2.5-4.5 in diameter, and coronary arteries are prospective target areas for the atherectomy devices taught herein.

Although it seems reasonable to simply increase the diameter of the cutter for larger blood vessels, the skilled artisan will realize that the diameter of the cutter can also be limited by physical complications of the patient's anatomy. For example, there can be complications that occur during surgery due to bleeding at the arterial puncture access, tortuous vessels, vessel size variations, and the like. The diameter of the cutter can range from about 0.70 mm to about 2.20 mm in some embodiments, 1.00 mm to 2.20 mm in some embodiments, 1.20 mm to 2.20 mm in some embodiments, 1.40 mm to 2.20 mm in some embodiments, 1.50 to 2.20 mm in some embodiments, or any range therein in increments of 0.10 mm. In some embodiments, the diameter of the cutter can be about 0.90 mm, 1.00 mm, 1.10 mm, 1.20 mm, 1.30 mm, 1.40 mm, 1.50 mm, 1.60 mm, 1.70 mm 1.80 mm, 1.90 mm, 2.00 mm, 2.10 mm, 2.20 mm, 2.30 mm, or any diameter therein, or range therein, in increments of 0.05 mm. This is significant, as blood vessel lumen diameters can be very small or quite large, and vessels having diameters of 1.00 mm are quite tight for cutters, and vessels having diameters over about 2.30 mm are becoming larger than a cutter can be made, in some embodiments. The skilled artisan will recognize that eccentric cutting allows for cutting a larger region than the diameter of the cutter assembly without adding or exchanging the cutter for other larger tools for removal. The cutter can be biased off-center within the larger blood vessels to clear a lumen that is larger than the diameter of the cutter.

The skilled artisan will also realize that the length of the cutter has to be limited to have the maneuverability needed. One of skill will realize that the size of the cutter can be any size known to be suitable in the art for the particular treatment. In some embodiments, the length of the cutter can range from about 0.50 mm to about 3.00 mm, from about 0.60 mm to about 2.80 mm, from about 0.80 mm to about 2.60 mm, from about 1.00 mm to about 2.40 mm, from about 1.00 mm to about 2.20 mm, from about 1.00 mm to about 2.00 mm, from about 1.20 mm to about 1.80 mm, or any range therein in increments of 0.10 mm.

The atherectomy device 200 further includes a drive assembly to drive the cutter 230. The drive assembly can have a flexible driveshaft 250 including a long axis having a central axis that can be coincident with the central axis 205 of the atherectomy device 200. The flexible driveshaft 250 can further have a proximal portion with a proximal end (not shown), a distal portion with a distal end 252, an outer surface 254, and a driveshaft lumen 256, the distal end 252 of the flexible drive shaft 250 having a fixed connection with the cutter 230. The flexible drive shaft 250 can be rotatably translational with the lumen 221 of the flexible sheath 215. The drive shaft 250 can extend to reach a driving engine located outside the subject receiving the atherectomy, the driving engine powered by an electric engine, in some embodiments, or powered by an air compressor in some embodiments, and the drive shaft 250 can be operably connected to a handle (not shown) at the proximal end of the atherectomy device for control by a user. The drive assembly can also have a positive displacement pump that pumps from the distal portion of the drive shaft 250 and adjacent to the helical flutes 238 at the proximal end of the cutter 230. In some embodiments, the positive displacement pump extends from the distal portion of the drive shaft 250 to the proximal portion of the driveshaft 250 to pump cut pieces of arterial plaque from a blood vessel.

One of skill will appreciate that the subject is a patient that is receiving the atherectomy. The term "subject" and "patient" can be used interchangeably and refer to an animal such as a mammal including, but not limited to, non-primates such as, for example, a cow, pig, horse, cat, dog, rabbit, rat and mouse; and primates such as, for example, a monkey or a human. The subject can also be a cadaver, in some embodiments, or a portion of a cadaver.

The flexible drive shaft 250 can be longer than the flexible sheath 215 to enable a reversible telescoping 270 of the drive assembly from the lumen 221 of the flexible sheath 215 at the distal end 252 of the flexible sheath 215. The guidewire lumen can include the cutter lumen 242 and the driveshaft lumen 256. Although the flexural stiffness of the drive shaft 250 remains the same between the collapsed and expanded states of the device, the flexural movement 290 increases upon the telescoping 270 of the drive shaft from the flexible sheath 215. As such, the amount of flexural movement 290 available is greater in FIG. 2A than in FIG. 2B, and the ease of flexural movement 290 is greater in FIG. 2A than in FIG. 2B due to the length of the drive shaft that has been telescoped in FIG. 2A as opposed to the length of the drive shaft exposed in FIG. 2B. We found that, as the amount and ease of flexural movement 290 increases due to the telescoping 270, the ease at which the cutter 230 can move through an artery increases.

In some embodiments, the cutter can be operably attached to the drive shaft using a friction fitting, so that the drive shaft is allowed slip on the base of the cutter when engaged with plaque and meeting a maximum torque limit. And, in some embodiments, the positive displacement pump can be a screw pump 280, also referred to as an Archimedes screw in some embodiments. The positive displacement pump can be attached to the outer surface 254 of the drive shaft 250, the distal end of the screw pump being adjacent to the helical flutes 238 at the proximal end 232 of the cutter 230 to transport pieces of cut plaque from the cutter in a distal to proximal direction to the proximal end of the atherectomy device for removal of the cut plaque from the subject.

Figure 3:
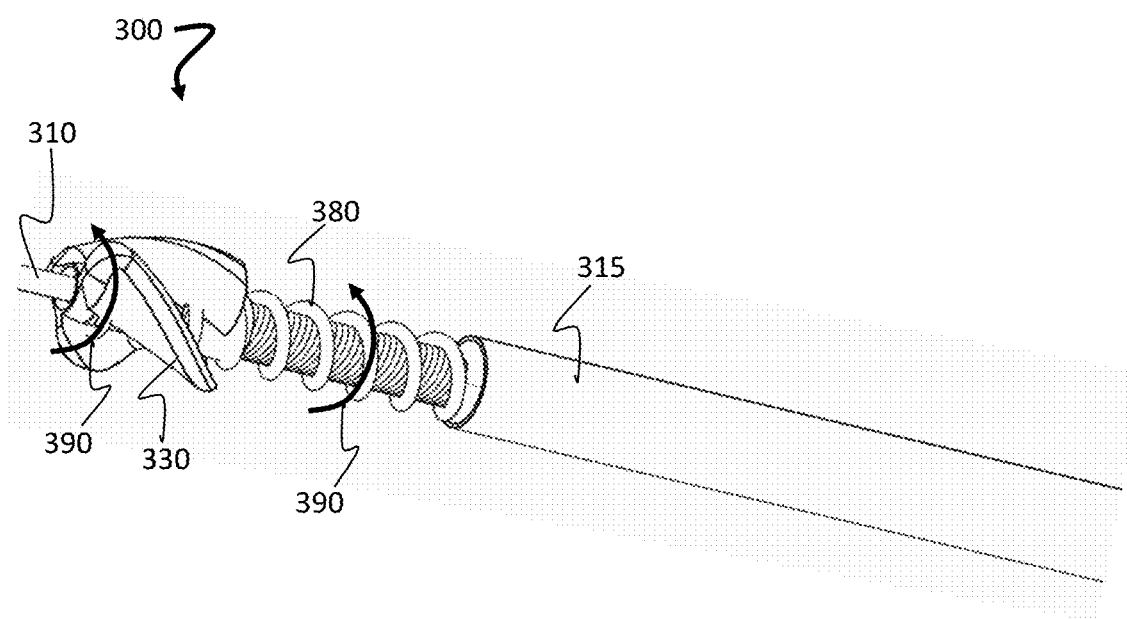
FIG. 3 illustrates a telescoping atherectomy device that can be self-driving, according to some embodiments.

FIG. 3 illustrates a telescoping atherectomy device that can be self-driving, according to some embodiments. The atherectomy device 300 can have a screw pump 380 in operable contact with a cutter 330, for example. The screw pump 380 can extend beyond the flexible sheath 315 and can be exposed for contact with a vascular lumen wall (not shown), often perhaps contact with remaining plaque on the lumen wall, during use of the atherectomy device within the vascular lumen. In some embodiments, the screw pump 380 can be a right hand screw (as shown) when the cutter 330 is rotated in the right-hand direction 390; and, in some embodiments, the screw pump 380 can be a left hand screw (opposite as shown) when the cutter 330 is rotated in the left-hand direction (opposite direction to 390). As such, a right-handed cutter can have a right-handed screw pump, and a left-handed cutter can have a left-handed screw pump, to enable the screw pump to assist in driving the atherectomy device 300 through the vascular lumen along the guidewire 310 during the cutting of the vascular plaque in the vascular lumen. One of skill will understand that a self-driving device can offer substantial value in that it can assist by reducing the forces needed from a surgeon, for example, during operation of the device. The self-driving can be all or partial, meaning that that the device can remove the need for the surgeon to push the device during the procedure, in some embodiments. And, in some embodiments, it eases the pressure required from the surgeon during the procedure. Those skilled in the art of atherectomy procedures will understand that pushing can cause the device to buckle, break, or jam; and/or, the patient can suffer complications through a perforation of a vessel receiving the treatment, as well as a perforation of a tissue surrounding the vessel receiving the treatment.

The self-driving feature of the atherectomy devices taught herein can reduce the pressure required from a surgeon performing the procedure. In some embodiments, the pressure required from the surgeon performing the atherectomy can be reduced by 100%, 95%, 90%, 85%, 80%, 75%, 70%, 65%, 60%, 55%, 50%, 45%, 40%, 35%, 30%, 25%, 20%, 15%, 10%, 5%, or any amount or range therein in increments of 1%. In some embodiments, the pressure required from the surgeon performing the atherectomy can be reduced in an amount ranging from about 25% to about 100%, from about 30% to about 100%, from about 35% to about 100%, from about 40% to about 100%, from about 45% to about 100%, from about 50% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, or any range therein in increments of 1%. Likewise, in some embodiments, the pressure required from the surgeon performing the atherectomy can be reduced in an amount ranging from about 25% to about 95%, from about 30% to about 90%, from about 35% to about 85%, from about 40% to about 80%, from about 45% to about 75%, from about 50% to about 70%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, or any range therein in increments of 1%. Likewise, in some embodiments, the pressure required from the surgeon performing the atherectomy can be reduced in an amount ranging from about 25% to about 50%, from about 50% to about 100%, or any range therein in increments of 1%. Likewise, in some embodiments, the pressure required from the surgeon performing the atherectomy can be reduced by at least 20%, at least 30%, at least 40%, at least 50%, at least 60%, at least 70%, at least 80%, at least 90%, or at least any range therein in increments of at 1%.

In some embodiments, a surgeon may need to apply a negative pressure, for example holding or pulling and not pushing, at times to aid control in the cutting of a lesion. It should be appreciated that the negative pressure can be a negative 1%, 5%, 10%, 15%, 20%, or 25%, or any amount therein in increments of 1%, in some embodiments. Such a negative pressure can result in slowing the forward movement of the cutting, stopping the cutting, or moving the cutting in a direction that opposes the self-driving direction of the cutter.

Those of skill in the art will appreciate that the atherectomy devices will offer a needed versatility and maneuverability in the art for tortuous blood vessels. When plaque is located in tortuous vessels or occluded eccentric to the passage of the vessel, eccentric cutting of the tissues can be useful to maneuver the cutting head to remove plaque. There have been atherectomy devices that offer a mechanism in the device that can create a curvature in the distal end of the device by pulling a "tendon" that pulls the end laterally. These devices suffer in that they create a "snapback" or "whip" motion of the device due to an imbalance of stresses being placed along the long axis of the atherectomy device. The devices provided herein provide eccentric cutting without the "snapback" or "whip" created by these earlier known mechanisms.

Figure 4A:
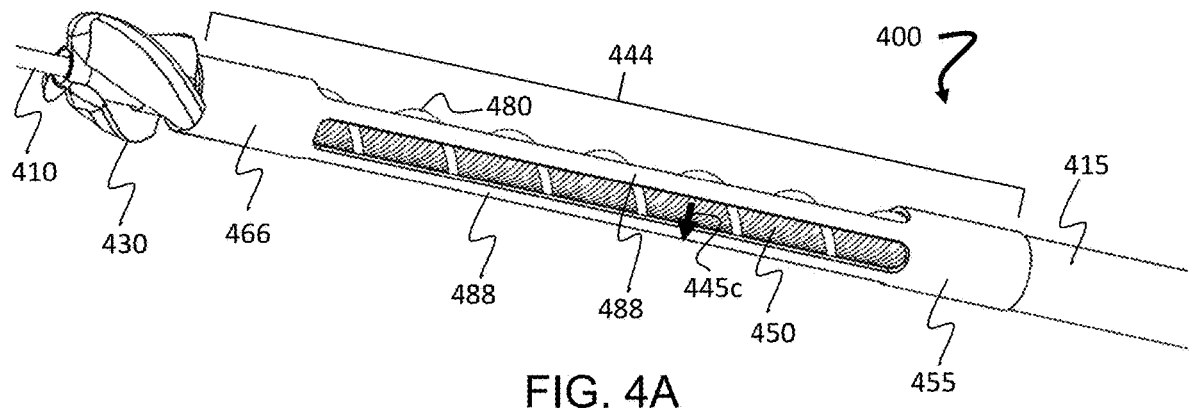
FIGS. 4A-4D illustrate a telescoping atherectomy device that can further comprise a reversibly-expandable, lateral pushing member at the distal end of the flexible sheath, wherein the expansion of the lateral pushing member induces a curve, according to some embodiments.
Figure 4B:
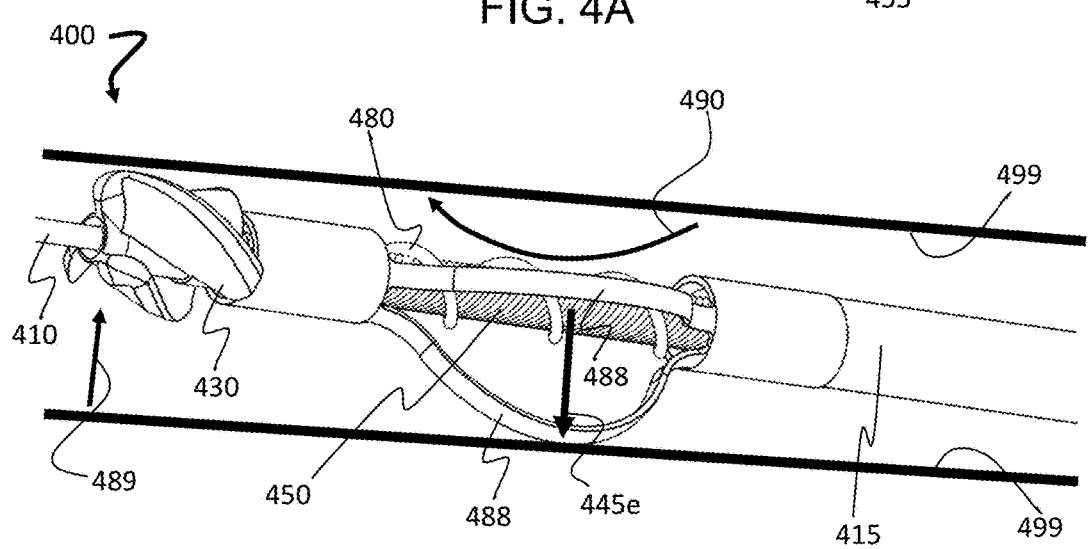
Figure 4C:
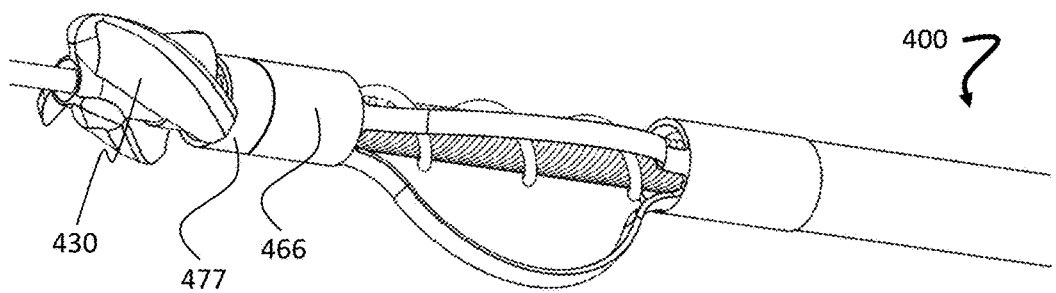

FIGS. 4A-4D illustrate a telescoping atherectomy device that can further comprise a reversibly-expandable, lateral pushing member at the distal end of the flexible sheath, wherein the expansion of the lateral pushing member induces a curve, according to some embodiments. As shown in FIG. 4A, the telescoping atherectomy device 400 can further comprise a reversibly-expandable, lateral pushing member 444 at the distal end of the flexible sheath 415, the pushing member 444 creating a lateral protrusion relative to the central axis of the atherectomy device. The lateral pushing member 444 can have a proximal portion with a proximal end, a distal portion with a distal end, and a reversibly-expandable portion having a collapsed state (as shown in FIG. 4A) and an expanded state (as shown in FIGS. 4B and 4C). The protrusion can be rotated relative to the lesion in any amount, from 1-360 degrees, or any range therein, for example, to reach any target area inside of a blood vessel.

The lateral pushing member can be made of any material known to be suitable by those of skill. For example, the lateral pushing member can be made of a flexible metal, a flexible metal that is biocompatible, such as titanium alloy such as Nickel Titanium. In some embodiments, the lateral pushing member can be made of a polymer such as PEEK, Polyimid or Nylon. The length of the trusses, or ribbon, can be designed to provide any desired protuberance. For example, the length of the trusses may vary from 1 mm-100 mm in some embodiments, 10 mm-30 mm in some embodiments, 10 mm to 40 mm in some embodiments, 10 mm to 50 mm in some embodiments, 20 mm to 60 mm in some embodiments, 20 mm to 80 mm in some embodiments, or any range therein. In some embodiments, the length of the trusses can be 1 mm, 2 mm, 4 mm, 6 mm, 8 mm, 10 mm, 12 mm, 14 mm, 16 mm, 18 mm, 20 mm, 30 mm, 40 mm, 50 mm, 60 mm, 70 mm, 80 mm, 100 mm, or any length therein in increments of 1 mm.

The reversibly-expandable portion has trusses 488 that expand and collapse the reversibly-expandable lateral pushing member 444 through the application of axial forces on the lateral pushing member 444. The trusses can be referred to as "ribbons", in some embodiments. The proximal end of the lateral pushing member 444 has an operable connection with the flexible sheath 415, and the distal end of the lateral pushing member 444 has an operable connection with the cutter 430. The operable connection with the flexible sheath 415 and the operable connection with the cutter 430 can each be configured to receive an axial force (i) applied along the axis of the flexible drive shaft 450 from the cutter 430 to the flexible sheath 415 and (ii) transferred through the lateral pushing member 444 to expand the lateral pushing member 444 when applying a distal to proximal axial force, and the collapse the lateral pushing member 444 when applying a proximal to distal axial force, the axial forces applied in the desired direction with the reversible telescoping action of the flexible drive shaft 450 within the flexible sheath 415. The lateral pushing member 444 has an effective radius upon collapse 445c and upon expansion 445e.

In some embodiments, proximal-to-distal and distal-to-proximal forces are received by the lateral pushing member 444 at a proximal collar 455 on the proximal portion of the lateral pushing member 444 and at a distal collar 466 on the distal portion of the lateral pushing member 444. Moreover, the operable connection between the lateral pushing member 444 and the cutter 430 can be configured as a rotatably translatable connection to facilitate a rotation of the cutter 430 and the flexible drive shaft 450 without rotating, or undesirably torquing, the distal end of the lateral pushing member 444 during operation of the atherectomy device 400.

The axial forces can be applied using any structure, a centralized member, for example a tendon, that applies the force along the central axis of the drive shaft to avoid inducing a load on the atherectomy device resulting in release of the snapback or whip forces along the long axis of the device. In some embodiments, the structure providing the axial force can be the drive shaft that is already located central to the device, for example, concentric within the sheath. As such, in some embodiments, the method of expanding the lateral pushing member includes applying a distal-to-proximal force to the distal portion of the lateral pushing member, the force applied along the central axis of the atherectomy device, the central axis of the drive shaft, or the central axis of the sheath.

The contact of the lateral pushing member 444 on the vessel wall laterally pushes the cutter 430 away from the central axis of the vessel lumen opposite direction of expansion of the trusses 488. The magnitude of the diversion of the cutter 430 is adjustable and controllable.

As shown in FIG. 4B, the expansion of the trusses 488 on the lateral pushing member 444 causes the cutter 430 of the atherectomy device 400 to deflect toward the vascular lumen wall 499 that is opposite the vascular lumen wall 499 receiving force from the expansion of the trusses 488.

One or more expandable trusses can be used. In some embodiments, there is a single truss. In some embodiments, there are 2 trusses. In some embodiments, there are 3 trusses. In some embodiments, there are 4 trusses. In some embodiments, there are at least 1, 2, 3, 4, 5, 6, 7, 8, 9, or 10 trusses. The trusses can be pre-shaped to create a biased curve or angle to protrude outwardly from the central axis of the device. That is, in some embodiments, the trusses have a shape memory that allows the trusses to remain in the collapsed state, and the expanded state is obtained by applying a force to the trusses, for example, by pulling on the central tendon, or drive shaft. In some embodiments, the trusses have a shape memory that allows the trusses to remain in the expanded state, and the collapsed state is maintained by holding the trusses in the collapsed state, and the expanded state is obtained by releasing that holding force and allowing the shape memory to return to the trusses. The trusses can be any shape and, in some embodiments, can be a single truss or a plurality of trusses. In some embodiments, the trusses can for a basket shape. In some embodiments, a balloon can be inflated to bias the cutter, rather than use a truss or trusses. For example, the trusses can be arched or angled ribbons, for example, that help to stabilize the flexible drive shaft.

The eccentric cutting of the devices provided herein can offer safe and clean cutting in tortuous and non-tortuous vessels, as well as eccentric lesions. The lateral pushing member 444 increases safety because, without such lateral protrusion, the cutter assembly is biased to move towards the outer side of the vessel curvature, which may accidently cut the vessel wall instead of the targeted plaque at the inner side of the vessel. The lateral pushing member 444 addresses that problem by correcting the bias by bulging the trusses 488 towards the outer side of the vessel curvature to laterally push the cutter to the opposite side of the blood vessel to achieve more controlled, effective, and safe cutting than conventional cutters. When debulking an eccentric lesion, for example, the adjustable lateral pushing enables the cutter assembly to target specifically towards the side of the vessel having the greater amount of the stenotic material to achieve eccentric cutting.

In some embodiments, the effective cutting diameter may be approximately half the diameter of the cutter plus the lateral extent of the protrusion from central axis of cutter. For example, if the cutter is 2.2 mm in diameter, and the protrusion is extended 3.0 mm from cutter axis, the effective cutting diameter is 4.1 mm. As can be seen, the eccentric cutting leads to a cutting area that is much larger than the diameter of the cutter.

The magnitude of the protrusion (from slightly protruded to maximally protruded) is adjustable, in some embodiments. For example, the distance between the two ends or collar of the lateral pushing member can be adjusted. That is, the distance between the two ends or collars of the lateral pushing member can be set as desired. In some embodiments, the distance between the collars is increased to reduce the expansion of the trusses and, thus, reduce the deflection of the cutter. Likewise, the distance between the collars can be decreased to increase the expansion of the trusses and, thus increase the deflection of the cutter. One of skill will appreciate that a dial, knob, button, or other actuator on the device can provide the user of the device with a measure of the distance between the collars of the lateral pushing member 444. In some embodiments, an increase in the distance that the drive shaft has moved relative to the sheath increases the expansion of the trusses 488. Likewise, in some embodiments, a decrease in the distance that the drive shaft has moved relative to the sheath decreases the expansion of the trusses 488.

In some embodiments, the proximal portion or proximal end of the lateral pushing member 444 will have a fixed contact with the distal portion or distal end of the sheath, and the distal portion or distal end of the drive shaft will have a rotatably translational connection with the cutter; with a component proximal to the cutter, the component including a race and a step to allow for rotation of the cutter despite the presence of the drive shaft. The race can be referred to as a "bearing surface" in some embodiments. The component can be, for example, a fixed race or bearing; and the like, such that the drive shaft freely rotates at the distal portion or distal end of the laterally pushing member while the laterally pushing member does not rotate.

Interestingly, it was discovered that the relative flexural stiffness of the drive shaft 450 as compared to the trusses 488 can also help control which portion of the cutter 430 makes contact with, and cuts, plaque on the vascular lumen wall 499. For example, if the flexural stiffness of the drive shaft 450 is greater than the flexural stiffness of the trusses 488, then the expansion of the trusses 488 will likely not cause a deformation 490 of the drive shaft 450, and the contact between the cutter 430 and the vascular lumen wall 499 will occur moreso on the side of the body of the cutter 430. However, if the flexural stiffness of the drive shaft 450 is less than the flexural stiffness of the trusses 488, the drive shaft 450 is expected to deform, and the contact between the cutter 430 and the vascular lumen wall 499 will begin to occur moreso toward the distal end of the cutter 430.

In some embodiments, the flexural stiffness of the distal portion of the flexible atherectomy device, $F_D$, is less than or equal to the flexural stiffness of the lateral pushing member, $F_{LPM}$. In some embodiments, the flexural stiffness of the distal portion of the flexible atherectomy device, $F_D$, is greater than or equal to the flexural stiffness of the lateral pushing member, $F_{LPM}$. In some embodiments, the flexural stiffness of the distal portion of the flexible atherectomy device, $F_D$, is greater than the flexural stiffness of the lateral pushing member, $F_{LPM}$.

$F_D$ can be reduced relative to $F_{LPM}$ by 75%, 70%, 65%, 60%, 55%, 50%, 45%, 40%, 35%, 30%, 25%, 20%, 15%, 10%, 5%, or any amount or range therein in increments of 1%. In some embodiments, $F_D$ can be reduced relative to $F_{LPM}$ in an amount ranging from about 25% to about 80%, from about 30% to about 75%, from about 35% to about 75%, from about 40% to about 75%, from about 45% to about 75%, from about 50% to about 75%, from about 60% to about 75%, from about 65% to about 75%, from about 70% to about 75%, or any range therein in increments of 1%. Likewise, in some embodiments, $F_D$ can be reduced relative to $F_{LPM}$ in an amount ranging from about 25% to about 50%, from about 30% to about 50%, from about 35% to about 50%, from about 40% to about 50%, from about 45% to about 50%, or any range therein in increments of 1%. Likewise, in some embodiments, $F_D$ can be reduced relative to $F_{LPM}$ in an amount ranging from about can be reduced by at least 20%, at least 30%, at least 40%, at least 50%, at least 60%, at least 70%, at least 80%, at least 90%, or at least any range or amount therein in increments of at 1%.

Given this information, one of skill will appreciate that the amount of deformation can be selected by selecting the relative ratios of flexural stiffness of the drive shaft 450 and the trusses 488, which will allow additional control of the cutter to the user of the atherectomy device. As such, in some embodiments, the atherectomy device 400 can be designed such that the flexural stiffness of the trusses 488 is greater than the flexural stiffness of the drive shaft 450 to obtain a desired amount of deflection of the drive shaft to direct a desired surface of the cutter 430 to the vascular lumen wall 499. In some embodiments, the flexural stiffness of the drive shaft can be equal to or greater than the flexural stiffness of the trusses 488 to avoid a deflection of the drive shaft. One of skill will appreciate that there are methods to vary the flexural stiffness of the drive shaft. The stiffness or flexibility of the drive shaft may be adjusted, for example, by varying the orientation or association of the filaments that compose the drive shaft. In some embodiments, to increase flexural stiffness, the filaments on the shaft can be bound together with stiffer material, or the flexural stiffness can be increased (or reduced) by increasing (or decreasing) the filament size.

The lateral pushing member can be designed to expand to a curved protuberance. In some embodiments, the lateral pushing member can collapse to have an effective radius 445c that is less than or equal to the radius of the sheath. In some embodiments, the lateral pushing member can collapse to have an effective radius 445c that is less than or equal to the radius of the cutter. In some embodiments, the lateral pushing member collapses to have an effective radius 445c that is less than or equal to the radius of the cleared diameter of the cutter to help facilitate movement of the device in the blood vessel.

Torsional stress on the lateral pushing member 444 is a design consideration. In order to reduce the concerns about the torsional stress induced on the lateral pushing member 444, the torsional stress on the distal end of the lateral pushing member can be reduced, the torsional stiffness of the lateral pushing member can be increased, or both of these design modifications can be implemented.

FIG. 4C provides an alternate operable connection between the cutter and the lateral pushing member to address torsional stresses, according to some embodiments. In some embodiments, the distal race is fixed and serves as a bearing race against the rotating cutter 430. In some embodiments, however, the distal race 477 rotates in contact with a rotating cutter 430 and the distal collar 466 of the lateral pushing member 444. As such, the distal race 477 can be freely rotating, in which the distal race 477 freely rotates to further reduce the torsional stress on the lateral pushing member 444. In some embodiments, the distal race 477 can be made of a low friction material, such as TEFLON.

Figure 4D:
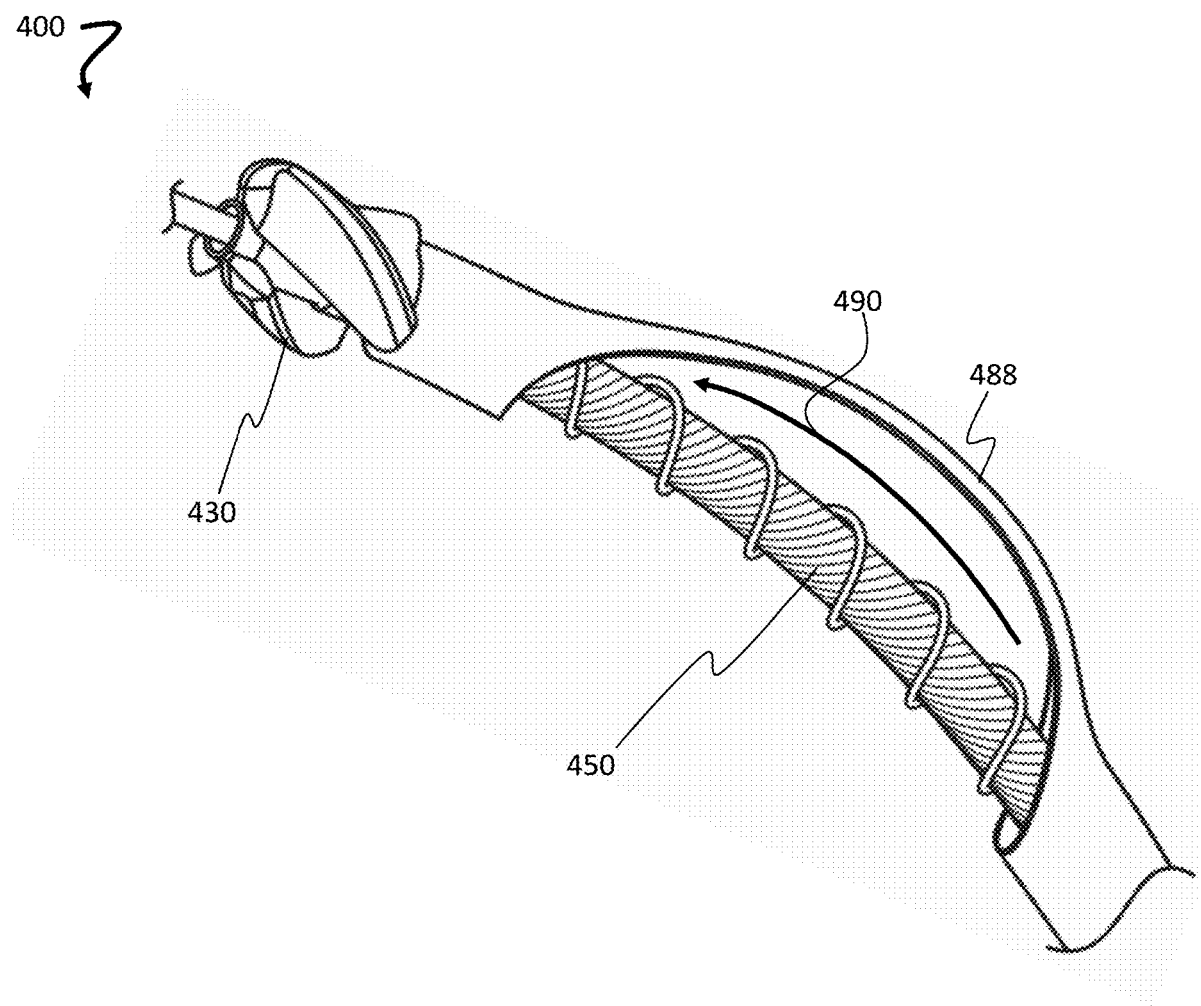

FIG. 4D illustrates how a curve can be induced in the distal portion of the atherectomy device as deformation 490. As discussed herein, the relative flexural stiffnesses of the distal portion of the drive shaft 450 and the lateral pushing member can induce the formation of the curve as force is applied to induce lateral expansion of trusses 488, as described above, also changing the orientation of the cutter 430 in the vessel lumen (not shown). The deformation 490 can be returned to a straight position as shown in FIB. 4B by telescoping the drive shaft 450 out from the sheath 415. This re-aligns the cutter 430 in the vessel lumen (not shown), from a position where the distal cutter is oriented to cut, to a position where the side of the cutter 430 is oriented to cut.

It should be appreciated that each of the telescoping feature, the self-driving feature, and the lateral pushing feature are distinct technical advantages. As such, the atherectomy device can be a self-driving atherectomy device only, meaning the device doesn't require telescoping or lateral pushing. In these embodiments, the components of which can be labeled the same or similar to the other embodiments taught herein, the device can have a distal portion with a distal end, a proximal portion with a proximal end, a long axis with a central axis, and a guidewire lumen passing through the device in the direction of the long axis. The device can include a flexible sheath having an outer diameter and a sheath lumen; a cutter having a proximal end, a distal end, and a body with a plurality of helical flutes. There can also be a point at the distal end of the cutter having a plurality of cutting lips, as well as a cutter lumen, and a cleared diameter. These devices also include a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a screw pump attached to the outer surface of the drive shaft and adjacent to the helical flutes at the proximal end of the cutter. The screw pump can include a drive screw portion. In some embodiments, the drive screw portion can be the distal portion of the screw pump.

To be self-driving, for example, the drive screw portion can extend beyond the flexible sheath and can be exposed for contact with a vascular lumen during use of the atherectomy device. To effectively assist in driving the device through the vascular lumen, the drive screw should turn in the same direction as the cutter. For example, if the flutes of the cutter spiral in the right hand direction the drive screw should spiral in the right hand direction. Likewise, if the flutes of the cutter spiral in the left hand direction the drive screw should spiral in the left hand direction. As such, in some embodiments, the drive screw portion can be a right hand screw when the cutter is rotated in the right-hand direction; and, in some embodiments, the drive screw portion can be a left hand screw when the cutter is rotated in the left-hand direction.

The relative size of the lumen, the cutter, and the drive screw can be designed to optimize the self-driving feature. In these embodiments, the cleared diameter of the cutter can be greater than the outer diameter of the flexible drive shaft; and, in some embodiments, the cleared diameter of the cutter can be greater than the outer diameter of the flexible sheath.

Of course, any of the self-driving devices can also include a telescoping feature, the components of which can be labeled the same or similar to the other embodiments taught herein. For example, the flexible drive shaft of the self-driving atherectomy device can be longer than the flexible sheath to enable a reversible telescoping of the drive assembly from the lumen of the flexible sheath at the distal end of the flexible sheath.

Moreover, any of the self-driving devices can also include a reversibly-expandable, lateral pushing member, the components of which can be labeled the same or similar to the other embodiments taught herein. In some embodiments, the lateral pushing member can have a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, in some embodiments, the operable connection with the cutter can be configured as a rotatably translatable connection to facilitate a rotation of the cutter and the flexible drive shaft without rotating the lateral pushing member, particularly the distal portion of the lateral pushing member, during operation of the atherectomy device.

Likewise, the atherectomy device can be a lateral pushing atherectomy device only, a device doesn't require self-driving, the components of which can be labeled the same or similar to the other embodiments taught herein. It does require telescoping, however, at least to the extent needed for an expanding and a collapsing of the lateral pushing member. In these embodiments, the device can have a distal end, a proximal end, a long axis, and a guidewire lumen passing through the device in the direction of the long axis. The device can include a flexible sheath having an outer diameter and a sheath lumen. The device can have a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, the lateral pushing atherectomy device can also have a reversibly-expandable, lateral pushing member at the distal end of the flexible sheath.

The relative size of the lumen and the cutter can be designed to optimize movement of the atherectomy device through the lumen. For example, the cleared diameter of the cutter can be greater than the outer diameter of the flexible drive shaft. In some embodiments, the cleared diameter of the cutter can be greater than the outer diameter of the flexible sheath. The size of the cutter lumen and the drive shaft lumen can be configured for passage of a guidewire of a desired gauge and, accordingly, the guidewire lumen can include the cutter lumen and the driveshaft lumen.

In some embodiments, the lateral pushing member can have a proximal portion with a proximal end, a distal portion with a distal end, a collapsed state, and an expanded state, the proximal end having an operable connection with the flexible sheath, and the distal end having an operable connection with the cutter. In some embodiments, the operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. And, in some embodiments, the operable connection with the cutter can be configured as a rotatably translatable connection to facilitate a rotation of the cutter and the flexible drive shaft without rotating the lateral pushing member during operation of the atherectomy device.

In some embodiments, atherectomy device can also be telescoping, the components of which can be labeled the same or similar to the other embodiments taught herein. That is, the flexible drive shaft of the laterally pushing atherectomy device can be longer than necessary for the expansion of the lateral pushing member. The flexible drive shaft of the laterally pushing atherectomy device can be longer than flexible sheath to enable a reversible telescoping of the drive assembly from the lumen of the flexible sheath at the distal end of the flexible sheath.

And, in some embodiments, the lateral pushing atherectomy device can also be self-driving, the components of which can be labeled the same or similar to the other embodiments taught herein. That is, the lateral pushing atherectomy device can comprise a drive screw attached to the outer surface of the distal end of the drive shaft and adjacent to the screw pump at the distal end of the screw pump. The drive screw can be a part of the screw pump, and it can extend beyond the flexible sheath and be exposed for contact with a vascular lumen during use. In some embodiments, the drive screw can be a right hand screw when the cutter is rotated in the right-hand direction; and, in some embodiments, the drive screw can be a left hand screw when the cutter is rotated in the left-hand direction.

We found that the ratios of (i) dimensions and (ii) stiffness of an atherectomy device taught herein each contribute to the performance and behavior of the device, the ease of advancement of the cutter, the ability to rotate the atherectomy device, the ability to steer the device, the relative amount of plaque removed, and the like. Table 2 provides example dimensions of the components of the atherectomy device, and Table 3 provides example ratios of the dimensions of the components of the atherectomy device.

TABLE 2

Examples of component dimension in mm.

| Cutter OD (mm) | Screw Pump OD (mm) | Drive Shaft OD (mm) | Sheath OD (mm) | Sheath ID (mm) | Minimum Front Cutting Diameter (mm) | Guidewire Lumen ID (mm) | Lateral Pushing Member OD (mm) |
|---|---|---|---|---|---|---|---|
| DESIGNED FOR LARGER ARTERIAL DIAMETERS |||||||| 
| 1.09-3.28 or 1.64-2.73 | 0.64-1.91 or 0.95-1.59 | 0.43-1.30 or 0.65-1.08 | 0.84-2.51 or 1.26-2.10 | 0.82-2.45 or 1.22-2.04 | 0.32-0.95 or 0.48-0.79 | 0.20-0.61 or 0.30-0.51 | 0.89-2.67 or 1.34-2.23 |
| DESIGNED FOR SMALLER ARTERIAL DIAMETERS ||||||||
| 0.70-2.10 or 1.05-1.75 | 0.51-1.52 or 0.76-1.27 | 0.43-1.30 or 0.65-1.08 | 0.69-2.06 or 1.03-1.71 | 0.65-1.95 or 0.98-1.63 | 0.32-0.95 or 0.48-0.79 | 0.20-0.61 or 0.30-0.51 | N/A |

TABLE 3

Examples of ratios of component dimensions

| Cutter OD: Screw Pump OD | Cutter OD: Sheath OD | Minimum Front Cutting Diameter: Cutter OD | Minimum Front Cutting OD: Guidewire Lumen ID | Screw Pump OD: Sheath ID | Screw OD: Drive Shaft OD | Cutter OD : Lateral Pushing Member OD |
|---|---|---|---|---|---|---|
| DESIGNED FOR LARGER ARTERIAL DIAMETERS |||||||
| 1.26-3.79 or 1.90-3.163 | 1.00-1.95 or 0.98-1.63 | 0.15-0.44 or 0.22-0.36 | 1.00-2.35 or 1.17-1.96 | 0.39-1.17 or 0.58-0.97 | 1.00-2.21 or 1.10-1.84 | 1.00-1.84 or 0.92-1.53 |
| DESIGNED FOR SMALLER ARTERIAL DIAMETERS |||||||
| 1.00-2.07 or 1.03-1.72 | 1.00-1.53 or 1.00-1.28 | 0.23-0.68 or 0.34-0.57 | 1.00-2.35 or 1.17-1.96 | 0.39-1.17 or 0.59-0.98 | 1.00-1.76 or 1.00-1.47 | N/A |

The "Cutter OD" is the largest outer diameter of the cutter.
The "Screw Pump OD" is the outer diameter of the drive shaft plus the two diameters of the screw pump wires surrounding the drive shaft.
The "Drive Shaft OD" is the outer diameter of the drive shaft and does not include the two diameters of the screw pump wires.
The "Sheath ID or OD" is the inner diameter or outer diameter of the flexible tube, or "sheath".
The "minimum front cutting OD" is the outer diameter of the most distal end of the cutter having cutting edges.
The "guidewire lumen ID" is the inner diameter of the guidewire lumen.
The "lateral pushing member OD" is the outer diameter of the lateral pushing member and can be taken in the collapsed state or the expanded state.

It was found that the relative sizes of the device component had a significant impact on the movement of the device within a vessel lumen. In some embodiments, the cutter diameter should be at least 30% greater than the drive shaft diameter. The ratio of cutter diameter to drive shaft diameter can range from 1.3 to 2.0 in some embodiments, 1.3 to 1.8 in some embodiments, 1.3 to 1.7 in some embodiments, 1.3 to 1.6 in some embodiments, 1.3 to 1.5 in some embodiments, 1.3 to 1.4 in some embodiments, or any range therein. In some embodiments, the ratio of cutter diameter to drive shaft diameter can be 1.3, 1.4, 1.5, 1.6, 1.7, 1.8, 1.9, 2.0, 2.1, 2.2, 2.3, 2.4, or 2.5, or any ratio therein in increments of 0.05, in some embodiments. In some embodiments, however, the cutter diameter is 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any percent therein in increments of 0.5%, greater than the drive shaft diameter.

In some embodiments, the cutter diameter should be at least 20% greater than the sheath. The ratio of cutter diameter to sheath diameter can range from 1.2 to 2.0 in some embodiments, 1.2 to 1.8 in some embodiments, 1.2 to 1.7 in some embodiments, 1.2 to 1.6 in some embodiments, 1.2 to 1.5 in some embodiments, 1.2 to 1.4 in some embodiments, 1.2 to 2.0 in some embodiments, or any range therein. In some embodiments, the ratio of cutter diameter to drive shaft diameter can be 1.2, 1.3, 1.4, 1.5, 1.6, 1.7, 1.8, 1.9, 2.0, 2.1, 2.2, 2.3, 2.4, or 2.5, or any ratio therein in increments of 0.05, in some embodiments. In some embodiments, however, the cutter diameter is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any percent therein in increments of 0.5%, greater than the sheath diameter.

The skilled artisan will appreciate that, given the teachings herein, the drive shaft, sheath and, in some embodiments, the lateral pushing member can be designed to have mechanical and physical properties that are desirable for the atherectomy procedure. In some embodiments, the mechanical and physical properties of the device provide adequate strength to push the cutter forward during the procedure yet flexible enough to maneuver and align the cutter with the guidewire in tortuous vessels.

One of skill will appreciate that the technology provided herein can include flexural stiffness design selections for components to facilitate enhanced performance, maneuverability, and reliability of the atherectomy devices. Flexural stiffness is a measure of deformability expressed in units of N/mm. For example, flexural stiffness may be described as the ability of the component to bend in response to an applied bending force without breaking or deforming the component. For example, one of skill may choose a flexural stiffness of the drive shaft, sheath, or both, in some embodiments, for maneuverability of the atherectomy device to follow a guide wire around tortuous vessels.

One of skill will also appreciate that the technology provided herein can include torsional stiffness design selections for components to facilitate enhanced performance through torsional strength. Torsional stiffness is resistance to twist from torsional loading, allowing the component to transmit a rotational load (torque) without untwisting, overtwisting, and/or deforming, and is in units of N*mm/rad. For example, one of skill may choose a torsional stiffness of the drive shaft, lateral pushing member or both, in some embodiments, to help ensure that the cutter can cut against resistance from the plaque without failure of the drive shaft, and the lateral pushing member doesn't rotate, or at least rotates only a limited amount, to avoid failure of the lateral pushing member device during the atherectomy procedure.

One of skill will also appreciate that the technology provided herein can include axial tensile stiffness design selections for components to facilitate enhanced performance through better response of the atherectomy devices to push and pull. Axial tensile stiffness is the resistance to stretch or contraction of along the length of the component under axial loading and is in units of N/mm. Key components that should include an axial tensile stiffness design selection include the drive shaft, the sheath, and the lateral pushing member.

Tables 4 and 5 provide examples of flexural stiffness, torsional stiffness, and axial stiffness of components of the atherectomy devices taught herein, as well as ratios of the relative stiffnesses of the components.

TABLE 4

Example component stiffnesses for the atherectomy devices.

| Drive Shaft Flexural Stiffness (N/mm) | Drive Shaft Torsional Stiffness (N*mm/rad) | Drive Shaft Axial Stiffness (N/mm) | Sheath Flexural Stiffness (N/mm) | Lateral Pushing Member Torsional Stiffness (N*mm/rad) | Lateral Pushing Member Axial Stiffness (N/mm) | Lateral Pushing Member Flexural Stiffness (N/mm) |
|---|---|---|---|---|---|---|
| 0.09-0.6 or 0.13-0.22 | 12.73-38.20 or 19.10-31.83 | 2.59-7.76 or 3.88-6.46- | 0.72-2.15 or 1.07-1.79 | 0.75-2.24 or 1.12-1.86 | 0.82-2.45 or 1.23-2.04 | 0.40-1.20 or 0.60-1.00 |

TABLE 5

Examples of ratios of the relative component stiffnesses for the atherectomy devices.

| Drive Shaft Flexural Stiffness: Sheath Flexural Stiffness | Drive Shaft Flexural Stiffness: Drive Shaft Torsional Stiffness | Drive Shaft Flexural Stiffness: Drive Shaft Axial Stiffness | Drive Shaft Torsional Stiffness: Drive Shaft Axial Stiffness | Lateral Pushing Member Torsional Stiffness: Lateral Pushing Member Axial Stiffness | Drive Shaft Axial Stiffness: Lateral Pushing Member Axial Stiffness | Drive Shaft Flexural Stiffness: Lateral Pushing Member Flexural Stiffness | Sheath Flexural Stiffness: Lateral Pushing Member Flexural Stiffness |
|---|---|---|---|---|---|---|---|
| 0.06-0.18 or 0.09-0.15 | 0.003-0.010 or 0.005-0.009 | 0.02-0.05 or 0.03-0.04 | 2.46-7.39 or 3.69-6.16 | 0.46-1.37 or 0.68-1.14 | 1.58-4.74 or 2.37-3.95 | 0.11-0.33 or 0.16-0.27 | 0.89-2.67 or 1.34-2.23 |

The flexural stiffness of the sheath should be at least 3× greater than the drive shaft, in some embodiments. The ratio of flexural stiffness of the drive shaft to the flexural stiffness of the sheath can range from 0.03 to 0.40 in some embodiments, 0.05 to 0.30 in some embodiments, 0.05 to 0.25 in some embodiments, 0.06 to 0.30 in some embodiments, or any range therein. In some embodiments, the ratio of flexural stiffness of the drive shaft to the flexural stiffness of the sheath can be 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40 or any ratio or range therein in increments of 0.005, in some embodiments. In some embodiments, however, the flexural stiffness of the sheath is 3×, 4×, 5×, 6×, 7×, 8×, 9×, 10×, or any range therein, greater than the flexural stiffness of the drive shaft.

Figure 5A:
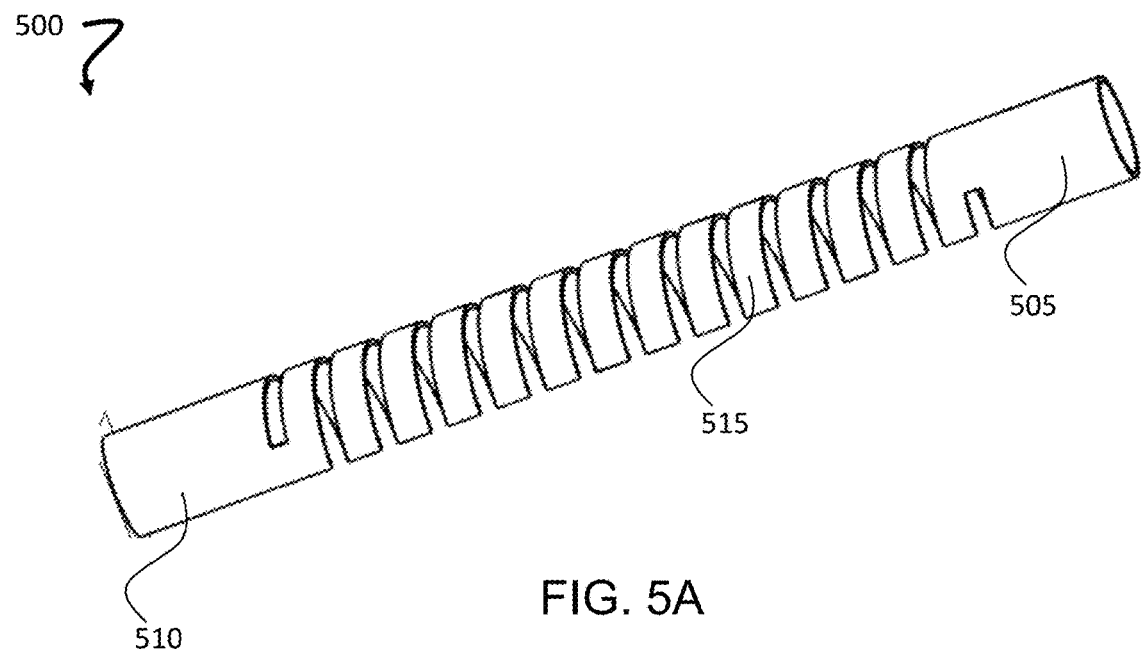
FIGS. 5A-5D illustrate a compressible sleeve that can be used to increase the torsional stiffness of the lateral pushing member, wherein the expansion of the lateral pushing member induces a curve, according to some embodiments.
Figure 5B:
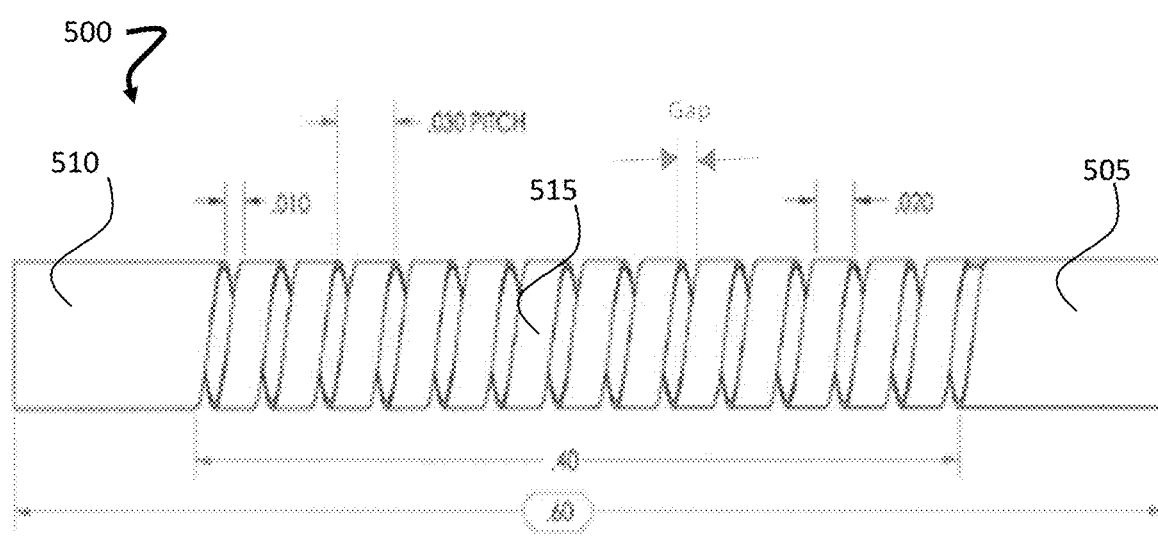
Figure 5C:
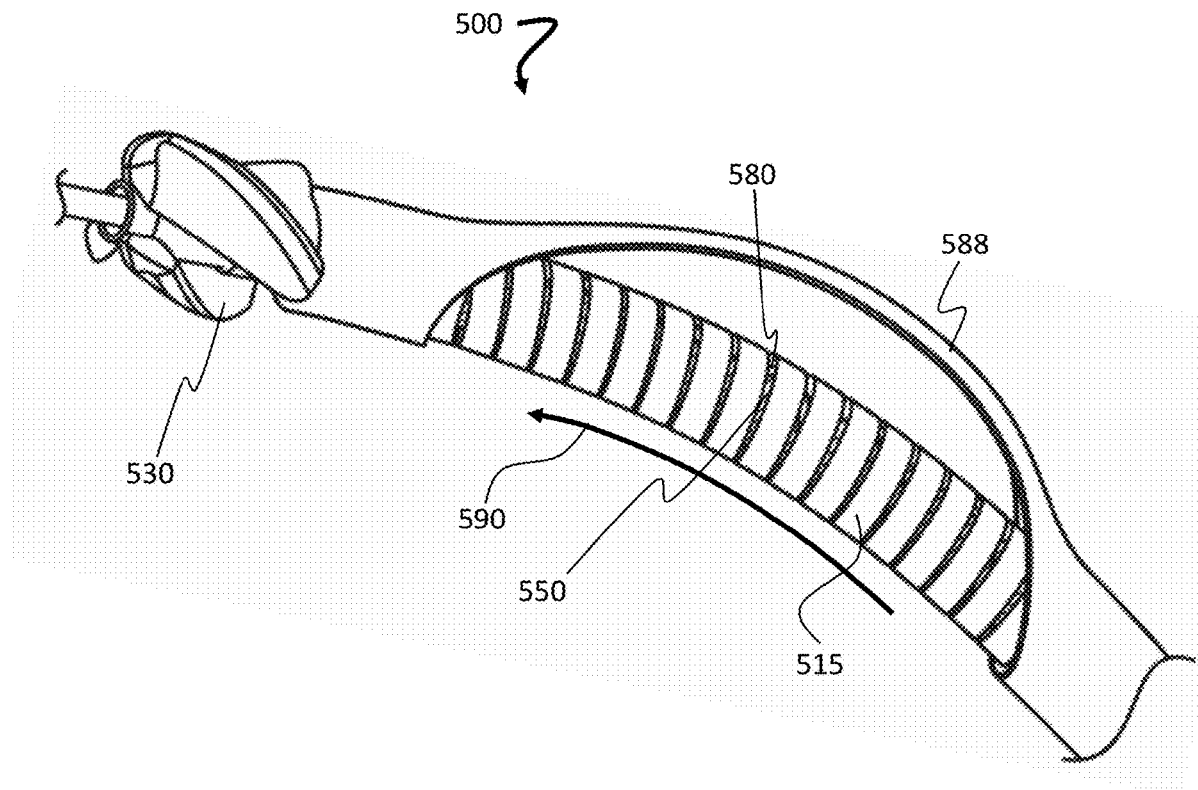

FIGS. 5A-5C illustrate a compressible sleeve that can be used to increase the torsional stiffness of the lateral pushing member, create a shield for the positive displacement pump, and increased the pumping efficiency to improve movement of cut particles out of the vessel, according to some embodiments. FIGS. 5A and 5B show that the compressible sleeve 500 has a proximal portion 505, a distal portion 510, and a compressible portion 515 having a spiral wound band that includes a gap between each of the spirals, a pitch between each of the spirals and a width and thickness of the spiral wound band. In some embodiments, the spiral wound band of the compressible portion 515 is integral with the proximal portion 505 and the distal portion 505.

FIG. 5C illustrates a deformation 590 of the distal portion of the atherectomy device. As discussed herein, the relative flexural stiffnesses of the distal portion of the drive shaft 550 and the trusses 588 in the lateral pushing member can induce the formation of the curve 590 as force is applied to induce lateral expansion of trusses 588, as described above, also changing the orientation of the cutter 630 in the vessel lumen (not shown). The compressible sleeve 500 compresses the spiral wound band of the compressible portion 515 during the lateral expansion of the trusses 588 and the creation of the deformation 590 of the drive shaft and compressible sleeve 500. As such, the expansion of the trusses 588 in the lateral pushing member can induce a curve 590 on the distal portion of the atherectomy device, according to some embodiments.

Figure 5D:
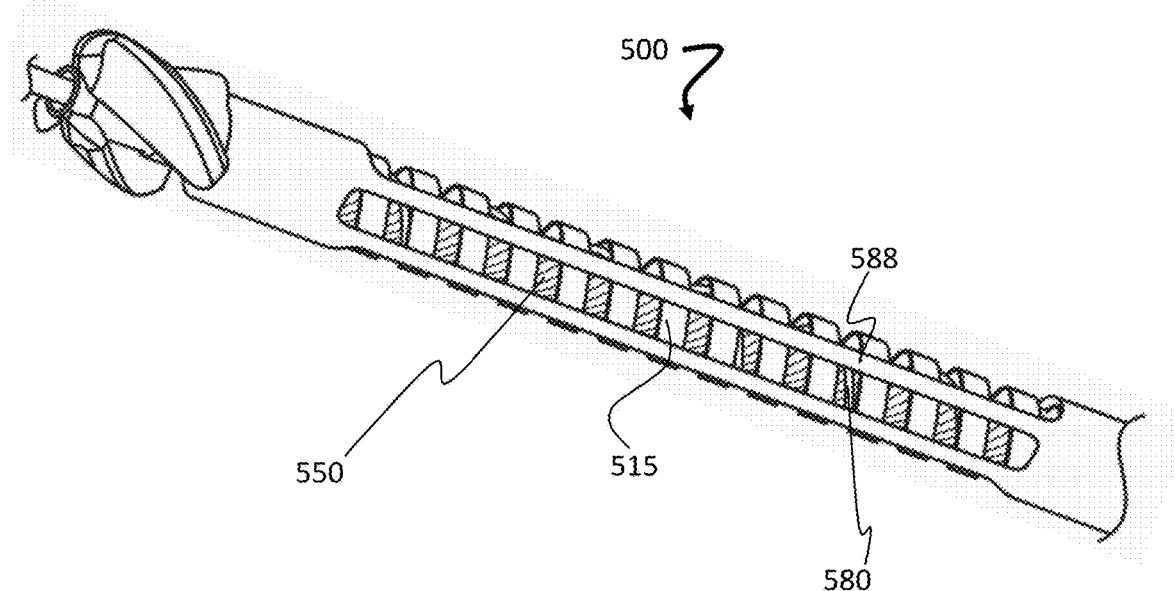

FIG. 5D illustrates a release of the deformation 590 of the distal portion of the atherectomy device to straighten the distal portion of the atherectomy device. The drive shaft 550 is telescoped out of the sheath (not shown) to relax the forces between the drive shaft 550 and trusses 588 and straighten the drive shaft 550 and trusses 588. This re-aligns the cutter 530 in the vessel lumen (not shown), from a position where the distal portion of the cutter 530 is oriented to cut, to a position where the side of the cutter 530 is oriented to cut. The compressible sleeve 500 relaxes and returns the spiral wound band of the compressible portion 515 from the deformation 590 caused by the lateral expansion of the trusses 588 to the original straight position as shown in FIG. 5D. As such, the expansion of the trusses 588 in the lateral pushing member can release deformation 590 on the distal portion of the atherectomy device and return to a straight position, according to some embodiments.

The compressible sleeve 500 can be placed outside of the flexible drive shaft and in-between the proximal and distal ends of the lateral pushing member, such that the flexible drive shaft 550 spins inside of the compressible sleeve. As shown herein, there can be a collar at each end of the laterally pushing member, a proximal collar and a distal collar, and the proximal portion 505 of the compressible sleeve 500 is operably attached to the proximal collar of the lateral pushing member, and the distal portion 510 of the compressible sleeve 500 is operably attached to the distal collar of the lateral pushing member. Due to the design of the compressible portion 515, the compressible sleeve 500 may be bent and compressed when the ribbons of the lateral pushing member protrude outwardly from a flat state while providing an added torsional stiffness between the proximal collar and the distal collar of the lateral pushing member to address torsion stresses on the lateral pushing member. In some embodiments, the distal and proximal collars of the lateral pushing member do not twist relative to each other, or any torsional movement is at least reduced. The compressible sleeve 500 also serves to cover the positive displacement pump, referred to as an Archimedes screw in some embodiments. As such, the compressible sleeve 500 can act as a safety shield during aspiration of the cut plaque particles with the Archimedes screw. And, it should be appreciated that having the cover over the positive displacement pump mechanism can assist the pump in the removal of particles by helping to retain the particles in a fixed space. For example, in the case of the screw pump, the compressible sleeve is in close proximity to the screw mechanism to retain plaque particles in the lumen of the compressible sleeve 500, helping the screw mechanism 580 move the particles out of the treated blood vessel with more efficiency.

Moreover, the expanded trusses 588 of the lateral pushing member require the proximal and distal collars of the lateral pushing member to move closer together when compressing the compressible sleeve 500, the compressing occurring in the gaps between the spirals of the compressible sleeve 500 to allow the shortening to occur.

The compressible sleeve 500 can be made of any suitable material known to one of skill, the choice of material dictating the required band width and thickness, for example. In some embodiments, the compressible sleeve may be made of stainless steel, Nitinol, other metal alloys, or polymers, PEEK, polycarbonate, nylon, or polyimide.

Example dimensions for the compressible sleeve 500 are listed in Table 6, at least for lower extremity vasculature,

TABLE 6

Dimensions of the compressible sleeve designed for use in vasculature"

| Outer Diameter OD (mm) | Inner Diameter ID (mm) | Pitch (mm) | Gap (mm) |
|---|---|---|---|
| 0.76-2.29 or 1.14-1.91 | 0.70-2.10 or 1.05-1.75 | 0.38-1.14 or 0.57-0.95 | 0.13-0.38 or 0.19-0.32 |

TABLE 7

Flexural and torsional stiffness of the drive shaft and compressible sleeve.

| Drive Shaft | | | Compressible Sleeve | | |
|---|---|---|---|---|---|
| Flexural Stiffness (N/mm) | Torsional Stiffness (N-mm/rad) | Axial Stiffness (N/mm) | Flexural Stiffness (N/mm) | Torsional Stiffness (N-mm/rad) | Axail Stiffness (N/mm) |
| 0.09-0.26 or 0.13-0.22 | 12.73-38.20 or 19.10-31.83 | 2.59-776 or 3.88-6.46 | 0.03-0.08 or 0.04-0.06 | 0.02-0.05 or 0.03-0.04 | 0.04-0.12 or 0.06-0.10 |

The stiffness and ratio of the drive shaft and the compressible sleeve are listed below in Tables 8 and 9:

TABLE 9

Ratio of the stiffness of the drive shaft and the compressible sleeve for vasculature

| Drive Shaft Axial Stiffness: Compressible Sleeve Axial Stiffness | Drive Shaft Flexural Stiffness: Compressible Sleeve Flexural Stiffness |
|---|---|
| >32.97 or >49.46 | 1.71-5.13 or 2.56-4.27 |

The flexural stiffness of the drive shaft should be at least 50% greater than the drive compressible sleeve, in some embodiments. The ratio of flexural stiffness of the drive shaft to the flexural stiffness of the compressible sleeve can range from 1.5 to 6.0 in some embodiments, 1.5 to 5.0 in some embodiments, 1.6 to 5.0 in some embodiments, 1.7 to 5.0 in some embodiments, or any range therein. In some embodiments, the ratio of flexural stiffness of the drive shaft to the flexural stiffness of the compressible sleeve can be 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, or any ratio or range therein in increments of 0.1, in some embodiments. In some embodiments, however, the flexural stiffness of the drive shaft is 2×, 3×, 4×, 5×, 6×, or any amount in increments of 0.1×, or any range therein, greater than the flexural stiffness of the compressible sleeve.

Figure 6A:
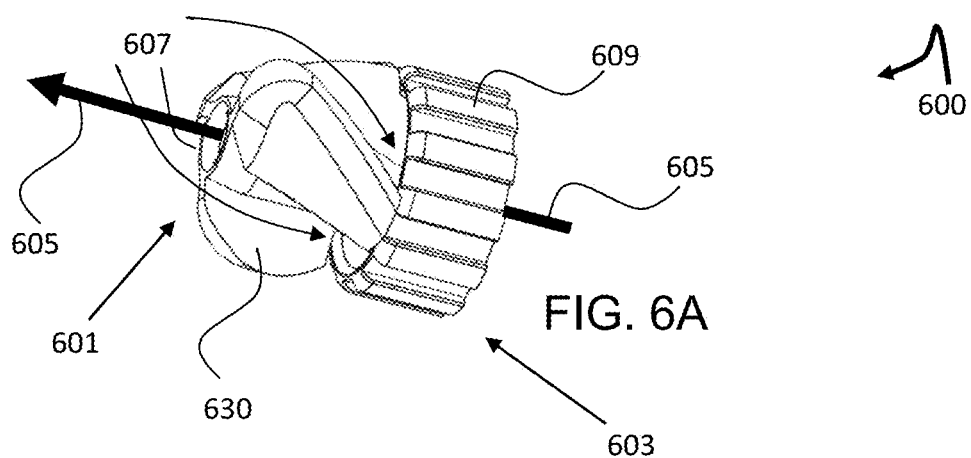
FIGS. 6A and 6B illustrate other cutters that may be used, according to some embodiments.
Figure 6B:
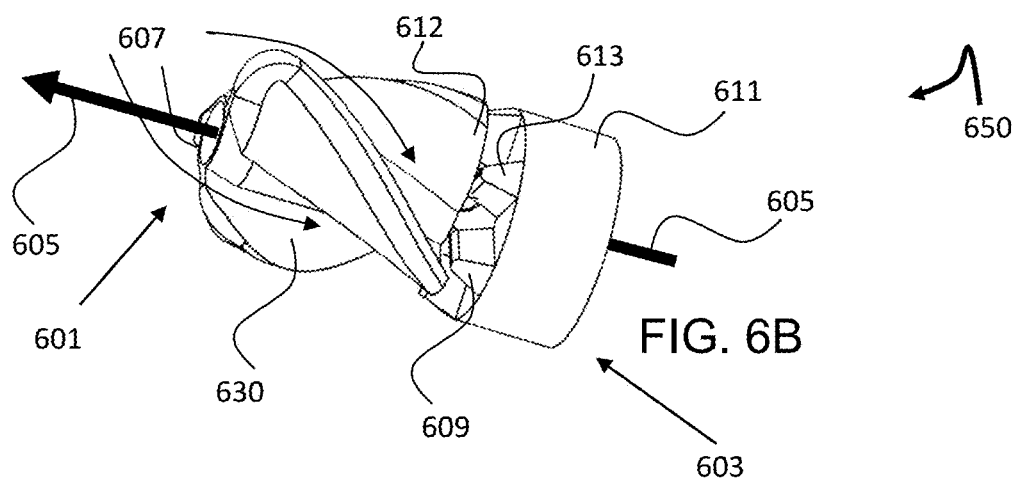

Although the performance of cutters can vary, depending on factors that include tissue type, for example, any cutter known to one of skill may be used with the atherectomy devices taught herein. FIGS. 6A and 6B illustrate other cutters that may be used, according to some embodiments. FIGS. 6A and 6B both show a cutter 600 having a distal end 601, proximal end 603, lumen 605, and flutes 607. The cutter 600 of FIG. 6A also has a burr portion 609, and the cutter 600 of FIG. 6B has a hammer portion 611.

The cutter in FIG. 6A has a burr portion 609 which can be fixed on the cutter, in some embodiments. In some embodiments, the burr portion 609 can be formed monolithically integral to the cutter. In some embodiments, however, the burr portion 609 can be operably attached to the cutter using a friction fitting, so that the burr is allowed slip on the base of the cutter when engaged with plaque and meeting a maximum torque limit.

The cutter in FIG. 6B has hammer portion 611 which can be fixed on the drive shaft, in some embodiments. In some embodiments, the hammer portion 611 can be operably attached to the cutter using a friction fitting, so that the hammer portion is allowed slip on the drive shaft when engaged with plaque and meeting a maximum torque limit. The hammer portion 611 has oscillating teeth 613 that contact the blade portion 612 to create an oscillating hammer effect on the plaque for cutting.

Atherectomy systems can also be assembled to include the atherectomy devices taught herein. In some embodiments, any of the atherectomy devices taught herein can be a system comprising the atherectomy device and a guidewire.

The atherectomy devices also lend to several methods of performing an atherectomy in a subject. In some embodiments, the methods can include creating a point of entry in a vascular lumen of the subject; inserting the atherectomy device into the vascular lumen; telescoping the flexible drive shaft; cutting a plaque from the vascular lumen with the cutter of the atherectomy device; discharging the cut plaque from the vascular lumen with the positive displacement pump; and, removing the atherectomy device from the vascular lumen of the subject.

In some embodiments, the methods can include creating a point of entry in a vascular lumen of the subject; inserting the atherectomy device into the vascular lumen; driving the atherectomy device through the vascular lumen with the exposed drive screw; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include creating a point of entry in a vascular lumen of the subject; inserting the atherectomy device into the vascular lumen; pushing the distal portion of the atherectomy device laterally in the vascular lumen, the pushing including expanding the lateral pushing member; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include grinding the plaque with a burr like, for example, the burr portion 609 of FIG. 6A. The burr can having ridges, like the burr portion 609, or it can be a grinding surface having a desired "grit".

Likewise, in some embodiments, the methods can include hammering the plaque with a hammering cutting blade configuration like, for example, the cutting portion 612 of the cutter of FIG. 6B.

One of skill will appreciate that the steps set-forth above represent only example of a series of steps that may be used in an atherectomy. In a simple embodiment, for example, the method includes inserting an atherectomy device taught herein into a vascular lumen of a subject, the atherectomy device having a distal end, a proximal end, a long axis, and a guidewire lumen passing through the device in the direction of the long axis;

a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath; and, a positive displacement pump that begins pumping at the distal end of the drive shaft and adjacent to the helical flutes at the proximal end of the cutter;

advancing the cutter to a target area in the vascular lumen of the subject, the advancing including telescoping the distal end of the flexible drive shaft away from the distal end of the flexible sheath to increase the flexibility of the atherectomy device in the vascular lumen; self-driving the cutter into the target region, the self-driving including turning a screw at the distal end of the flexible drive shaft;

laterally pushing the distal end of the flexible sheath, distal end of the flexible drive shaft, and the cutter against the wall of the vascular lumen; or, a combination thereof;

cutting plaque away from the wall of the vascular lumen, the cutting including rotating the cutter; and, removing the plaque from the vascular lumen using the positive displacement pump; and, removing the atherectomy device from the subject.

It should be appreciated that the devices, systems and methods provided herein allow for enhanced functionality during an atherectomy procedure. In some embodiments, a method of steering a cutting head are provided, and these methods can include redirecting the distal end of the flexible atherectomy device. In some embodiments, the redirecting can include (i) expanding the pushing member, the expanding including pulling a centralized "member"

(ii) wherein the expanding expands the lateral pushing member to push and bend/curve the distal end of the flexible atherectomy device.

The centralized "member" can be, for example, either the flexible drive shaft, or perhaps a centralized tendon that is also freely translatable in the axial direction, meaning translatable in the longitudinal axis direction, and perhaps even forming the guidewire lumen in some embodiments. A truly surprising and unexpected benefit was provided by the centralized pull on or near the central axis of the atherectomy device, central axis of the sheath, and or central axis of the drive shaft. To reiterate this surprising result, prior art Telescoping, self-driving, and laterally-pushing atherectomy devices are provided, each having a flexible sheath, a cutter with helical flutes, and a drive assembly. The drive assembly can have a flexible driveshaft that is rotatably translational with the lumen of the flexible sheath, a positive displacement pump that begins pumping at the distal end of the drive shaft adjacent to the helical flutes at the proximal end of the cutter, and the flexible drive shaft can be longer than the flexible sheath to enable a reversible telescoping of the drive assembly from the lumen of the flexible sheath. The positive displacement pump can be a screw pump having a drive screw portion extending beyond the flexible sheath, exposed for contact with a vascular lumen for the self-driving. And, the devices can have a reversibly-expandable, lateral pushing member at the distal end of the flexible sheath for the lateral pushing.

We claim:

1. An atherectomy device, comprising:
a distal end, a proximal end, a long axis, and a guidewire lumen passing through the device in the direction of the long axis;
a flexible sheath having an outer diameter and a sheath lumen;
a cutter having a proximal end, a distal end, and a body with a plurality of helical flutes, a point at the distal end having a plurality of cutting lips, a cutter lumen, and a cleared diameter; and, a drive assembly having
a flexible drive shaft including an axis, a proximal end, a distal end, an outer surface, and a drive shaft lumen, the distal end of the flexible drive shaft having a fixed connection with the cutter, wherein the flexible drive shaft is rotatably translational within the lumen of the flexible sheath;
a positive displacement pump that begins pumping at the distal end of the drive shaft and adjacent to the helical flutes at the proximal end of the cutter;
wherein,
the cleared diameter of the cutter is greater than the outer diameter of the flexible drive shaft;
the flexible drive shaft is longer than the flexible sheath to enable a reversible telescoping of the drive assembly from the lumen of the flexible sheath at the distal end of the flexible sheath;
the guidewire lumen includes the cutter lumen and the drive shaft lumen;
and, the positive displacement pump is a screw pump, and the screw pump
extends beyond the flexible sheath and is exposed for contact with a vascular lumen during use of the atherectomy device within the vascular lumen;
is a right hand screw when the cutter is rotated in the right-hand direction; or,
is a left hand screw when the cutter is rotated in the left-hand direction.

2. The atherectomy device of claim 1, further comprising a reversibly-expandable, lateral pushing member at the distal end of the flexible sheath.

3. A system comprising the atherectomy device of claim 1 and a guidewire.

4. The atherectomy device of claim 3, wherein the cleared diameter of the cutter is greater than the outer diameter of the flexible sheath.

5. The atherectomy device of claim 3, wherein the screw pump is attached to the outer surface of the drive shaft, the distal end of the screw pump being adjacent to the helical flutes at the proximal end of the cutter.

6. A method of performing an atherectomy in a subject using the atherectomy device of claim 3, the method comprising
creating a point of entry in a vascular lumen of the subject;
inserting the guidewire into the vascular lumen;
inserting the atherectomy device into the vascular lumen over the guidewire;
telescoping the flexible drive shaft;
cutting a plaque from the vascular lumen with the cutter of the atherectomy device;
discharging the cut plaque from the vascular lumen with the positive displacement pump; and,
removing the atherectomy device from the vascular lumen of the subject.

7. A method of performing an atherectomy in a subject using the atherectomy device of claim 1, the method comprising
creating a point of entry in a vascular lumen of the subject;
inserting the atherectomy device into the vascular lumen;
telescoping the flexible drive shaft;
cutting a plaque from the vascular lumen with the cutter of the atherectomy device;
discharging the cut plaque from the vascular lumen with the positive displacement pump; and,
removing the atherectomy device from the vascular lumen of the subject.

8. The atherectomy device of claim 1, wherein the cleared diameter of the cutter is greater than the outer diameter of the flexible sheath.

9. The atherectomy device of claim 1, further comprising a reversibly-expandable, lateral pushing member at the distal end of the flexible sheath, the lateral pushing member having a proximal end, a distal end, a collapsed state, and an expanded state, the proximal end having a connector assembly with the flexible sheath, and the distal end having a connector assembly with the cutter; wherein,
the connector assembly with the flexible sheath and the connector assembly with the cutter are each configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath; and,
the connector assembly with the cutter is configured as a rotatably translatable connection to facilitate a rotation of the cutter and the flexible drive shaft without rotating the lateral pushing member during operation of the atherectomy device.

10. A system comprising the atherectomy device of claim 9 and a guidewire.

11. An atherectomy device, comprising:
a distal end, a proximal end, a long axis, and a guidewire lumen passing through the device in the direction of the long axis;
a flexible sheath having an outer diameter and a sheath lumen;
a cutter having a proximal end, a distal end, and a body with a plurality of helical flutes, a point at the distal end having a plurality of cutting lips, a cutter lumen, and a cleared diameter;

a drive assembly having
a flexible driveshaft including an axis, a proximal end, a distal end, an outer surface, and a driveshaft lumen, the distal end of the flexible drive shaft having a fixed connection with the cutter, wherein the flexible drive shaft is rotatably translational within the lumen of the flexible sheath;
a positive displacement pump that begins pumping at the distal end of the drive shaft and adjacent to the helical flutes at the proximal end of the cutter; and,
a reversibly-expandable, lateral pushing member at the distal end of the flexible sheath, the lateral pushing member having a proximal end, a distal end, a collapsed state, and an expanded state, the proximal end having a connector assembly with the flexible sheath, and the distal end having a connector assembly with the cutter;
wherein,
the cleared diameter of the cutter is greater than the outer diameter of the flexible drive shaft;
the flexible drive shaft is longer than the flexible sheath to enable a reversible telescoping of the drive assembly from the lumen of the flexible sheath at the distal end of the flexible sheath;
the guidewire lumen includes the cutter lumen and the driveshaft lumen;
the connector assembly with the flexible sheath and the connector assembly with the cutter are each configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath; and,
the connector assembly with the cutter is configured as a rotatably translatable connection to facilitate a rotation of the cutter and the flexible drive shaft without rotating the lateral pushing member during operation of the atherectomy device.

12. A method of performing an atherectomy in a subject using the atherectomy device of claim 11, the method comprising
creating a point of entry in a vascular lumen of the subject;
inserting the atherectomy device into the vascular lumen;
telescoping the flexible drive shaft;
cutting a plaque from the vascular lumen with the cutter of the atherectomy device;
discharging the cut plaque from the vascular lumen with the positive displacement pump; and,
removing the atherectomy device from the vascular lumen of the subject.

13. The atherectomy device of claim 11, wherein the cleared diameter of the cutter is greater than the outer diameter of the flexible sheath.

14. The atherectomy device of claim 11, wherein the positive displacement pump is a screw pump attached to the outer surface of the drive shaft, the distal end of the screw pump being adjacent to the helical flutes at the proximal end of the cutter.

15. The atherectomy device of claim 11, wherein the positive displacement pump is a screw pump, and the screw pump
extends beyond the flexible sheath and is exposed for contact with a vascular lumen during use of the atherectomy device within the vascular lumen; and,
is a right hand screw when the cutter is rotated in the right-hand direction; or,
is a left hand screw when the cutter is rotated in the left-hand direction.

16. A system comprising the atherectomy device of claim 15 and a guidewire.

17. A system comprising the atherectomy device of claim 11 and a guidewire.

\* \* \* \* \*